United States Patent
Meng et al.

(10) Patent No.: US 10,662,254 B2
(45) Date of Patent: May 26, 2020

(54) HINGE MODIFIED ANTIBODY FRAGMENTS AND METHODS OF MAKING

(71) Applicant: GENENTECH, INC., South San Francisco, CA (US)

(72) Inventors: Yu-Ju G. Meng, South San Francisco, CA (US); Hok Seon Kim, South San Francisco, CA (US); Ingrid Kim, South San Francisco, CA (US); Christoph Spiess, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/967,154

(22) Filed: Apr. 30, 2018

(65) Prior Publication Data

US 2018/0305462 A1  Oct. 25, 2018

Related U.S. Application Data

(63) Continuation of application No. PCT/US2016/059137, filed on Oct. 27, 2016.

(60) Provisional application No. 62/248,792, filed on Oct. 30, 2015, provisional application No. 62/346,905, filed on Jun. 7, 2016.

(51) Int. Cl.
*C07K 16/42* (2006.01)

(52) U.S. Cl.
CPC ...... *C07K 16/4283* (2013.01); *C07K 2317/34* (2013.01); *C07K 2317/52* (2013.01); *C07K 2317/53* (2013.01); *C07K 2317/54* (2013.01); *C07K 2317/55* (2013.01); *C07K 2317/71* (2013.01); *C07K 2317/75* (2013.01); *C07K 2317/76* (2013.01); *C07K 2317/94* (2013.01)

(58) Field of Classification Search
CPC ............ C07K 16/4283; C07K 2317/53; C07K 2317/34; C07K 2317/54; C07K 16/00
See application file for complete search history.

(56) References Cited

U.S. PATENT DOCUMENTS

| | | |
|---|---|---|
| 4,816,567 A | 3/1989 | Cabilly et al. |
| 5,208,020 A | 5/1993 | Chari et al. |
| 5,416,064 A | 5/1995 | Chari et al. |
| 5,635,483 A | 6/1997 | Pettit et al. |
| 5,648,237 A | 7/1997 | Carter |
| 5,712,374 A | 1/1998 | Kuntsmann et al. |
| 5,714,586 A | 2/1998 | Kunstmann et al. |
| 5,739,116 A | 4/1998 | Hamann et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,789,199 A | 8/1998 | Joly et al. |
| 5,840,523 A | 11/1998 | Simmons et al. |
| 5,877,296 A | 3/1999 | Hamann et al. |
| 5,959,177 A | 9/1999 | Hein et al. |
| 6,040,498 A | 3/2000 | Stomp et al. |
| 6,171,586 B1 | 1/2001 | Lam et al. |
| 6,267,958 B1 | 7/2001 | Andya et al. |
| 6,417,429 B1 | 7/2002 | Hein et al. |
| 6,420,548 B1 | 7/2002 | Vézina et al. |
| 6,630,579 B2 | 10/2003 | Chari et al. |
| 7,125,978 B1 | 10/2006 | Vézina et al. |
| 7,498,298 B2 | 3/2009 | Doronina et al. |
| 8,273,352 B2 * | 9/2012 | Huang ............ C07K 16/18 424/133.1 |
| 2005/0260186 A1 | 2/2005 | Bookbinder et al. |
| 2006/0104968 A1 | 5/2006 | Bookbinder et al. |
| 2013/0060011 A1* | 3/2013 | Bruenker ............ C07K 16/468 530/387.3 |
| 2014/0227259 A1* | 8/2014 | Ashman ............ C07K 16/00 424/133.1 |

FOREIGN PATENT DOCUMENTS

| | | | |
|---|---|---|---|
| EP | 0 425 235 B1 | 9/1996 | |
| WO | WO 94/11026 A2 | 5/1994 | |
| WO | WO 00/42072 A2 | 7/2000 | |
| WO | WO 2004/092219 A2 | 10/2004 | |
| WO | WO 2006/044908 A2 | 4/2006 | |
| WO | WO-2009011941 A2 * | 1/2009 | ......... C07K 16/1081 |
| WO | WO-2013024059 A2 * | 2/2013 | ............ C07K 16/00 |

OTHER PUBLICATIONS

Van Schie et al., mAbs 7(4): 662-671 (Year: 2015).*
Belaaouaj et al., "Degradation of Outer Membrane Protein A in *Escherichia coli* Killing by Neutrophil Elastase," Science 289:1185-1188 (2000).
Bos et al., "Development of a semi-automated high throughput transient transfection system," Journal of Biotechnology 180:10-16 (2014).
Brezski et al., "Immunoglobulin isotype knowledge and application to Fc engineering," Curr. Opin. Immunol. 40:62-69 (2016).
Brezski et al., "Cleavage of IgGs by proteases associated with invasive diseases: An evasion tactic against host immunity?" mAbs 2(3):212-220 (2010).
Brezski et al., "A monoclonal antibody against hinge-cleaved IgG restores effector function to proteolytically-inactivated IgGs in vitro and in vivo," mAbs 6(5):1265-1273 (2014).
Brezski et al., "Human Anti-IgG1 Hinge Autoantibodies Reconstitute the Effector Functions of Proteolytically Inactivated IgGs," J Immunol. 181:3183-3192 (2008).
Brezski et al., "The in vitro resistance of IgG2 to proteolytic attack concurs with a comparative paucity of autoantibodies against peptide analogs of the IgG2 hinge," mAbs 3(6):558-567 (2011).

(Continued)

*Primary Examiner* — Phuong Huynh
(74) *Attorney, Agent, or Firm* — Baker Botts L.L.P.

(57) ABSTRACT

The instant disclosure provides antibody fragments (e.g., Fab and F(ab')$_2$) having reduced or no reactivity towards pre-existing anti-hinge antibodies (AHA) and compositions comprising such antibody fragments, as well as methods of making and using such antibody fragments and compositions.

10 Claims, 20 Drawing Sheets

Specification includes a Sequence Listing.

(56) References Cited

OTHER PUBLICATIONS

Capel et al., "Heterogeneity of Human IgG Fc Receptors," Immunomethods 4:25-34 (1994).
Carter et al., "High level *Escherichia coli* expression and production of a bivalent humanized antibody fragment," Nature Biotechnology 10:163-167 (1992).
Chari et al., "Immunoconjugates Containing Novel Maytansinoids: Promising Anticancer Drugs," Cancer Res. 52:127-131 (1992).
Charlton, "Expression and Isolation of Recombinant Antibody Fragments in *E. coli*" Chapter 14 in Methods in Molecular Biology. Antibody Engineering, vol. 248 (B.K.C. Lo, ed., Humana Press, Totowa, NJ, 2004), pp. 245-254.
Chen et al., "Selection and Analysis of an Optimized Anti-VEGF Antibody: Crystal Structure of an Affinity-matured Fab in Complex with Antigen," J Mol. Biol. 293:865-881 (1999).
Cordy et al., "Specificity of human anti-variable heavy (VH) chain autoantibodies and impact on the design and clinical testing of a VH domain antibody antagonist of TNF-α receptor 1," Clin Exp Immunol. 182:139-148 (2015).
Curtis et al., "Thrombocytopenia after second exposure to abciximab is caused by antibodies that recognize abciximab-coated platelets," Blood 99:2054-2059 (2002).
Daëron, "Fc Receptor Biology," Annu. Rev. Immunol. 15:203-234 (1997).
De Haas et al., "Fcγ receptors of phagocytes," J. Lab. Clin Med. 126(4):330-341 (1995).
Desjarlais et al., "Modulation of antibody effector function," Experimental Cell Research 317:1278-1285 (2011).
Dubowchik et al., "Doxorubicin Immunoconjugates Containing Bivalent, Lysosomally-Cleavable Dipeptide Linkages," Bioorg. & Med. Chem. Letters 12:1529-1532 (2002).
Eaton et al., "Construction and Characterization of an Active Factor VIII Variant Lacking the Central One-Third of the Molecule," Biochemistry 25(26):8343-8347 (1986).
Ellerman et al., "Generation of Bispecific Antibodies by Chemical Conjugation," in Bispecific Antibodies, (Kontermann, R. E. ed.), pp. 47-63, Springer-Verlag Berlin Heidelberg, (2011).
Flatman et al., "Process analytics for purification of monoclonal antibodies," J. Chromatography B 848:79-87 (2007).
Gadkar et al., "Design and Pharmacokinetic Characterization of Novel Antibody Formats for Ocular Therapeutics," Invest. Ophthalmol. Vis. Sci. 56(9):5390-5400 (2015).
Gerngross, "Advances in the production of human therapeutic proteins in yeasts and filamentous fungi," Nat. Biotech. 22(11):1409-1414 (2004).
Ghetie et al., "FcRn: the MHC class I-related receptor that is more than an IgG transporter," Immunol. Today 18(12):592-598 (1997).
Ghetie et al., "Increasing the serum persistence of an IgG fragment by random mutagenesis," Nature Biotechnology, 15:637-640 (1997).
Glennie et al., "Preparation and Performance of Bispecific F(ab' γ)2 Antibody Containing Thioether-Linked Fab'γ Fragments," J Immunol. 139:2367-2375 (1987).
Graham et al., "Characteristics of a Human Cell Line Transformed by DNA from Human Adenovirus Type 5," J. Gen Virol. 36:59-72 (1977).
Guyer et al., "Immunoglobulin Binding by Mouse Intestinal Epithelial Cell Receptors," J. Immunol. 117(2):587-593 (1976).
Hinman et al., "Preparation and Characterization of Monoclonal Conjugates of the Calicheamicins: A Novel and Potent Family of Antitumor Antibiotics," Cancer Res. 53:3336-3342 (1993).
Hinton et al., "Engineered Human IgG Antibodies with Longer Serum Half-lives in Primates," J. Biol. Chem. 279(8):6213-6216 (2004).
Jacobsen et al., "Molecular and Functional Characterization of Cynomolgus Monkey IgG Subclasses," J Immunol. 186:341-349 (2011).
Jeffrey et al., "Dipeptide-based highly potent doxorubicin antibody conjugates," Bioorganic & Med Chem. Letters 16:358-362 (2006).
Jones et al., "A rheumatoid factor paradox: inhibition of rituximab effector function," Arthritis Res. Ther. 15:R20 (2013).
Kabat et al., Sequences of Proteins of Immunological Interest, 5th Ed. Public Health Service, National Institutes of Health, Bethesda, MD, 1991.
Kim et al., "Localization of the site of the murine IgG1 molecule that is involved in binding to the murine intestinal Fc receptor," Euro J. Immunol. 24:2429-2434 (1994).
King et al., "Monoclonal Antibody Conjugates of Doxorubicin Prepared with Branched Peptide Linkers: Inhibition of Aggregation by Methoxytriethyleneglycol Chains," J. Med. Chem. 45:4336-4343 (2002).
Kostelny et al., "Formation of a Bispecific Antibody by the Use of Leucine Zippers," J. Immunol. 148(5):1547-1553 (1992).
Kratz et al., "Prodrugs of Anthracyclines in Cancer Chemotherapy," Current Med. Chem. 13:477-523 (2006).
Li et al., "Optimization of humanized IgGs in glycoengineered Pichia pastoris," Nat. Biotech. 24(2):210-215 (2006).
Lode et al., "Targeted Therapy with a Novel Enediyene Antibiotic Calicheamicin $\theta^1$ Effectively Suppresses Growth and Dissemination of Liver Metastases in a Syngeneic Model of Murine Neuroblastoma," Cancer Res. 58:2925-2928 (1998).
Malia et al., "Structure and specificity of an antibody targeting a proteolytically cleaved IgG hinge," Proteins 82:1656-1667 (2014).
Mather et al., "Culture of Testicular Cells in Hormone-Supplemented Serum-Free Medium," NYAS 383:44-68 (1982).
Mather, "Establishment and Characterization of Two Distinct Mouse Testicular Epithelial Cell Lines," Biol. Reprod. 23:243-252 (1980).
Mellbye et al., "Evidence for Immune Complexes containing Antibody to the Pepsin Site of IgG in Rheumatoid Synovial Fluids," Clin Exp Immunol. 8:889-899 (1971).
Nagy et al., "Stability of cytotoxic luteinizing hormone-releasing hormone conjugate (AN-152) containing doxorubicin 14-O-hemiglutarate in mouse and human serum in vitro: Implications for the design of preclinical studies," PNAS USA 97(2):829-834 (2000).
Nisonoff et al., "Properties of the Major Component of a Peptic Digest of Rabbit Antibody," Science 132:1770-1771 (1960).
Olafsen, "Fc Engineering: Serum Half-Life Modulation through FcRn Binding," Methods Mol Biol. 907:537-556 (2012).
Osterland et al., "Anti-γ-Globulin Factors in Human Sera Revealed by Enzymatic Splitting of Anti-Rh Antibodies," Vox Sang. 8:133-152 (1963).
Pollack et al., "Idarucizumab for Dabigatran Reversal," N. Engl. J. Med. 373:511-520 (2015).
Porter, "The Formation of a Specific Inhibitor by Hydrolysis of Rabbit Antiovalbumin," Biochem J. 46:479-484 (1949).
Ravetch et al., "Fc Receptors," Annu. Rev. Immunol. 9:457-492 (1991).
Rispens et al., "Antibodies to constant domains of therapeutic monoclonal antibodies: Anti-hinge antibodies in immunogenicity testing," J Immunol Methods. 375:93-99 (2012).
Shields et al., "High Resolution Mapping of the Binding Site on Human IgG1 for FcγRI, FcγRII, FcγRIII, and FcRn and Design of IgG1 Variants with Improved Binding to the FcγR," J. Biol. Chem. 276(9):6591-6604 (2001).
Simmons et al., "Expression of full-length immunoglobulins in *Escherichia coli*: rapid and efficient production of aglycosylated antibodies," J Immunol Methods 263:133-147 (2002).
Spiess et al., "Alternative molecular formats and therapeutic applications for bispecific antibodies," Mol. Immunol. 67:95-106 (2015).
Terness et al., "The natural human IgG anti-F(ab')2 antibody recognizes a conformational IgG1 hinge epitope," J Immunol. 154:6446-6452 (1995).
Torgov et al., "Generation of an Intensely Potent Anthracycline by a Monoclonal Antibody-β-Galactosidase Conjugate," Bioconj. Chem. 16:717-721 (2005).
Urlaub et al., "Isolation of Chinese hamster cell mutants deficient in dihydrofolate reductase activity," PNAS USA 77(7):4216-4220 (1980).
Van Schie et al., "Cross-reactive and pre-existing antibodies to therapeutic antibodies—Effects on treatment and immunogenicity," mAbs 7(4):662-671 (2015).

(56) References Cited

OTHER PUBLICATIONS

Vincents et al., "Enzymatic Characterization of the Streptococcal Endopeptidase, IdeS, Reveals that it is a Cysteine Protease with Strict Specificity for IgG Cleavage Due to Exosite Binding," Biochemistry 43:15540-15549 (2004).
Vitetta et al., "Redesigning Nature's Poisons to Create Anti-Tumor Reagents," Science 238:1098-1104 (1987).
Von Pawel-Rammingen et al., "IdeS, a novel streptococcal cysteine proteinase with unique specificity for immunoglobulin G," The EMBO J. 21(7):1607-1615 (2002).
Walsh, "Biopharmaceutical benchmarks 2014," Nat Biotechnol. 32(10):992-1000 (2014).
Wong et al., "Enhancement of DNA Uptake in FUT8-Deleted CHO Cells for Transient Production of Afucosylated Antibodies," Biotechnol Bioeng. 106(5):751-763 (2010).
Yazaki and Wu, "Expression of Recombinant Antibodies in Mammalian Cell Lines" Chapter 15 in Methods in Molecular Biology, vol. 248 (B.K.C Lo, ed., Humana Press, Totowa, NJ), pp. 255-268 (2003).

\* cited by examiner

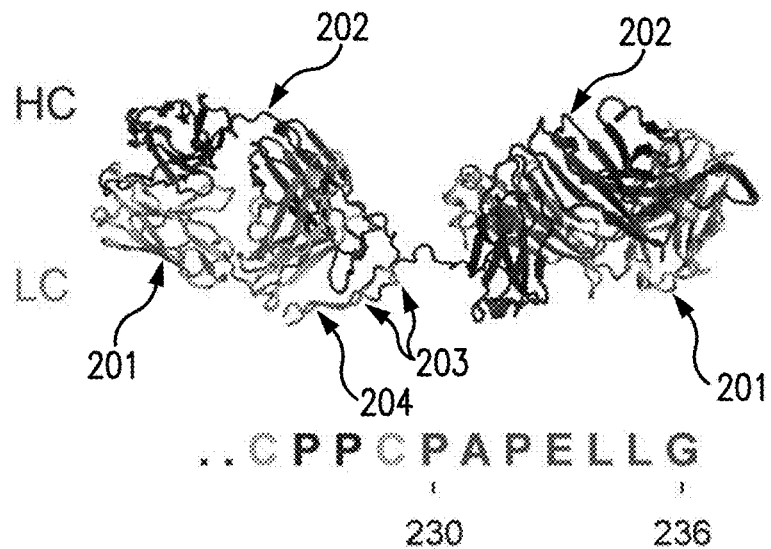
FIG. 2A
```
IgG1:    . . C P P C P A P E L L G G P S V
IgG1-z:  . . C P P C P A P P V A - G P S V
```
FIG. 2B
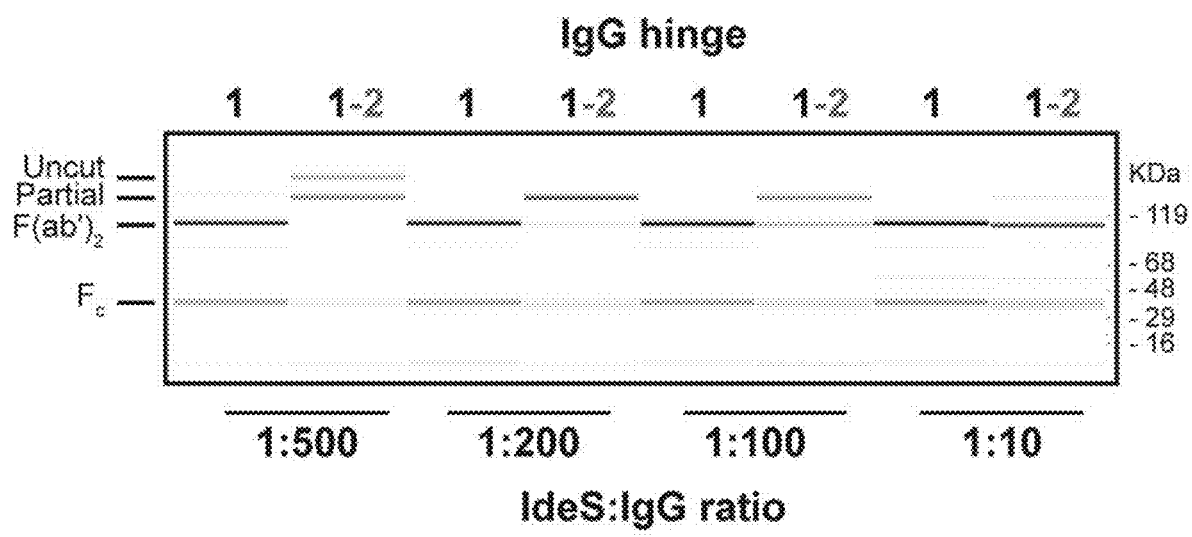
FIG. 2C

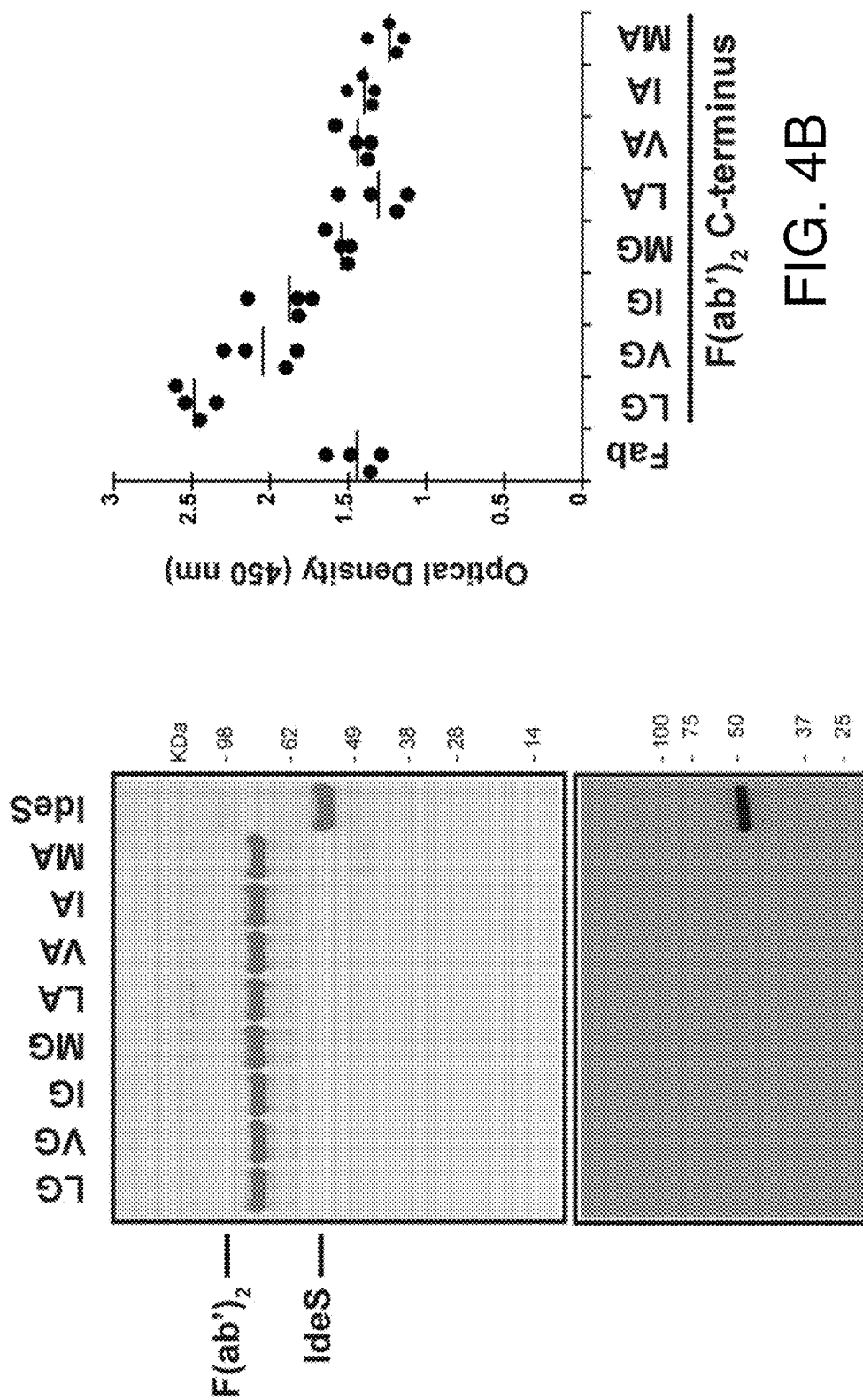

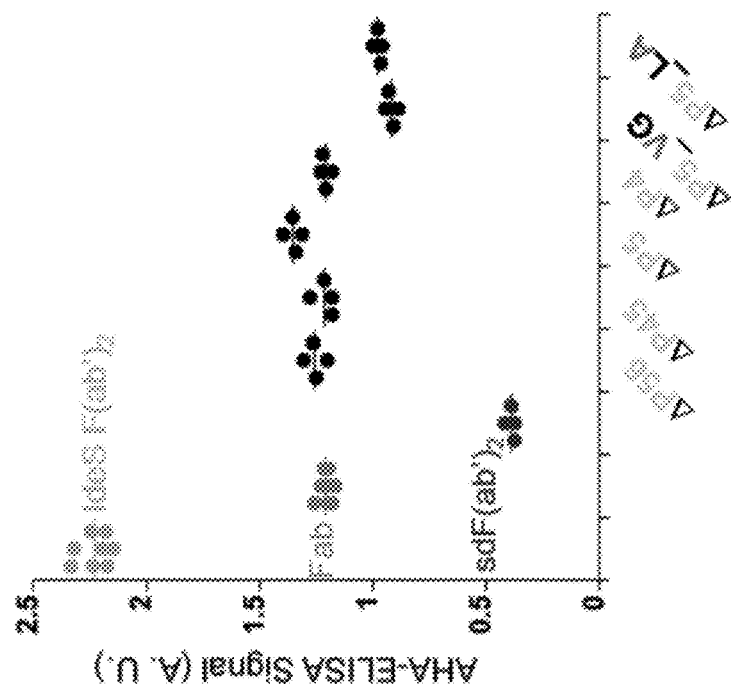
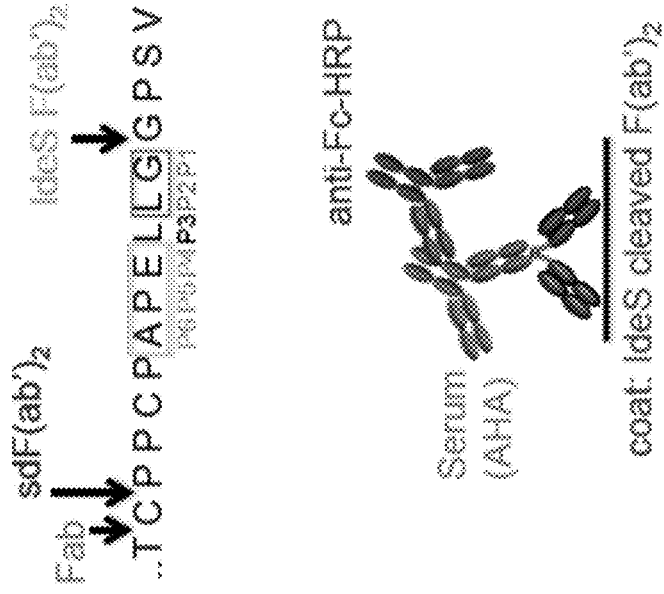
FIG. 9D

SEQUENCE LISTING

```
<160> NUMBER OF SEQ ID NOS: 59

<210> SEQ ID NO 1
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr
            100                 105

<210> SEQ ID NO 2
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Leu
            100                 105
```

<210> SEQ ID NO 3
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His
            100                 105
```

<210> SEQ ID NO 4
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95
```

Lys Val Glu Pro Lys Ser Cys Asp Lys Thr
            100                 105

<210> SEQ ID NO 5
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys
            100                 105

<210> SEQ ID NO 6
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp
            100

<210> SEQ ID NO 7
<211> LENGTH: 101
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys
            100

<210> SEQ ID NO 8
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro
            100                 105

<210> SEQ ID NO 9
<211> LENGTH: 103
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly
            100

<210> SEQ ID NO 10
<211> LENGTH: 104
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro
            100

<210> SEQ ID NO 11
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro
            100                 105

<210> SEQ ID NO 12
<211> LENGTH: 102

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr
            100

<210> SEQ ID NO 13
<211> LENGTH: 101
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys
            100

<210> SEQ ID NO 14
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Cys Asp Lys Thr His Thr
1               5
```

```
<210> SEQ ID NO 15
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Cys Asp Lys Thr His Leu
1               5

<210> SEQ ID NO 16
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Cys Asp Lys Thr His
1               5

<210> SEQ ID NO 17
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Cys Asp Lys Thr
1

<210> SEQ ID NO 18
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Lys Tyr Gly Pro Pro
1               5

<210> SEQ ID NO 19
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Lys Tyr Gly Pro
1

<210> SEQ ID NO 20
<211> LENGTH: 5
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 20

Asp Lys Thr His Leu
1               5

<210> SEQ ID NO 21
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Asp Lys Thr His Thr
1               5

<210> SEQ ID NO 22
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Glu Pro Lys Ser Cys Asp Lys Thr His Thr
1               5                   10

<210> SEQ ID NO 23
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Cys Pro Pro Cys
1

<210> SEQ ID NO 24
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Pro Ala Pro Glu Leu Leu Gly Gly Pro
1               5

<210> SEQ ID NO 25
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: MOD_RES
<222> LOCATION: (6)..(6)
<223> OTHER INFORMATION: Any amino acid except Thr

<400> SEQUENCE: 25

Cys Asp Lys Thr His Xaa
1               5

<210> SEQ ID NO 26
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Val Glu Arg Lys
1

<210> SEQ ID NO 27
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Asp Lys Thr His
1

<210> SEQ ID NO 28
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gly His His His His His
1               5

<210> SEQ ID NO 29
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

His His His His His
1               5

<210> SEQ ID NO 30
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 30

Cys Pro Pro Cys Pro Ala Pro Glu Leu Leu Gly
1               5                   10

<210> SEQ ID NO 31
<211> LENGTH: 15
<212> TYPE: PRT
<213> ORGANISM: Homo sapiens

<400> SEQUENCE: 31

Cys Pro Pro Cys Pro Ala Pro Glu Leu Leu Gly Gly Pro Ser Val
1               5                   10                  15

<210> SEQ ID NO 32
<211> LENGTH: 14
<212> TYPE: PRT
<213> ORGANISM: Homo sapiens

<400> SEQUENCE: 32

Cys Pro Pro Cys Pro Ala Pro Pro Val Ala Gly Pro Ser Val
1               5                   10

<210> SEQ ID NO 33
<211> LENGTH: 15
<212> TYPE: PRT
<213> ORGANISM: Homo sapiens

<400> SEQUENCE: 33

Cys Pro Arg Cys Pro Ala Pro Glu Leu Leu Gly Gly Pro Ser Val
1               5                   10                  15

<210> SEQ ID NO 34
<211> LENGTH: 15
<212> TYPE: PRT
<213> ORGANISM: Homo sapiens

<400> SEQUENCE: 34

Cys Pro Ser Cys Pro Ala Pro Glu Phe Leu Gly Gly Pro Ser Val
1               5                   10                  15

<210> SEQ ID NO 35
<211> LENGTH: 23
<212> TYPE: PRT
<213> ORGANISM: Homo sapiens

<400> SEQUENCE: 35

Lys Val Glu Pro Lys Ser Cys Asp Lys Thr His Thr Cys Pro Pro Cys
1               5                   10                  15

Pro Ala Pro Glu Leu Leu Gly
            20

<210> SEQ ID NO 36
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Cys Pro Pro Cys Pro Ala Pro Glu Leu Gly Gly Pro Ser Val
1               5                   10
```

```
<210> SEQ ID NO 37
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Cys Pro Pro Cys Pro Ala Pro Leu Leu Gly Gly Pro Ser Val
1               5                   10

<210> SEQ ID NO 38
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Cys Pro Pro Cys Pro Ala Glu Leu Leu Gly Gly Pro Ser Val
1               5                   10

<210> SEQ ID NO 39
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Cys Pro Pro Cys Pro Ala Pro Leu Gly Gly Pro Ser Val
1               5                   10

<210> SEQ ID NO 40
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Cys Pro Pro Cys Pro Ala Leu Leu Gly Gly Pro Ser Val
1               5                   10

<210> SEQ ID NO 41
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Cys Pro Pro Cys Pro Leu Leu Gly Gly Pro Ser Val
1               5                   10

<210> SEQ ID NO 42
<211> LENGTH: 11
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Cys Pro Pro Cys Leu Leu Gly Gly Pro Ser Val
1               5                   10

<210> SEQ ID NO 43
<211> LENGTH: 23
<212> TYPE: PRT
<213> ORGANISM: Homo sapiens

<400> SEQUENCE: 43

Glu Pro Lys Ser Cys Asp Lys Thr His Thr Cys Pro Pro Cys Pro Ala
1               5                   10                  15

Pro Glu Leu Leu Gly Gly Pro
            20

<210> SEQ ID NO 44
<211> LENGTH: 26
<212> TYPE: PRT
<213> ORGANISM: Macaca fascicularis

<400> SEQUENCE: 44

Glu Ile Lys Thr Cys Gly Gly Gly Ser Lys Pro Pro Thr Cys Pro Pro
1               5                   10                  15

Cys Pro Ala Pro Glu Leu Leu Gly Gly Pro
            20                  25

<210> SEQ ID NO 45
<211> LENGTH: 26
<212> TYPE: PRT
<213> ORGANISM: Macaca mulatta

<400> SEQUENCE: 45

Glu Ile Lys Thr Cys Gly Gly Gly Ser Lys Pro Pro Thr Cys Pro Pro
1               5                   10                  15

Cys Pro Ala Pro Glu Leu Leu Gly Gly Pro
            20                  25

<210> SEQ ID NO 46
<211> LENGTH: 19
<212> TYPE: PRT
<213> ORGANISM: Homo sapiens

<400> SEQUENCE: 46

Glu Arg Lys Cys Cys Val Glu Cys Pro Pro Cys Pro Pro Pro Val
1               5                   10                  15

Ala Gly Pro

<210> SEQ ID NO 47
<211> LENGTH: 19
<212> TYPE: PRT
<213> ORGANISM: Macaca fascicularis

<400> SEQUENCE: 47

Gly Leu Pro Cys Arg Ser Thr Cys Pro Pro Cys Pro Ala Glu Leu Leu
1               5                   10                  15

Gly Gly Pro
```

```
<210> SEQ ID NO 48
<211> LENGTH: 19
<212> TYPE: PRT
<213> ORGANISM: Macaca mulatta

<400> SEQUENCE: 48

Gly Leu Pro Cys Arg Ser Thr Cys Pro Pro Cys Ala Glu Leu Leu
1               5                   10                  15

Gly Gly Pro

<210> SEQ ID NO 49
<211> LENGTH: 67
<212> TYPE: PRT
<213> ORGANISM: Homo sapiens

<400> SEQUENCE: 49

Glu Leu Lys Thr Pro Leu Gly Asp Thr Thr His Thr Cys Pro Glu Pro
1               5                   10                  15

Lys Ser Cys Asp Thr Pro Pro Pro Cys Pro Arg Cys Pro Glu Pro Lys
            20                  25                  30

Ser Cys Asp Thr Pro Pro Pro Cys Pro Arg Cys Pro Glu Pro Lys Ser
        35                  40                  45

Cys Asp Thr Pro Pro Pro Cys Pro Arg Cys Pro Ala Pro Glu Leu Leu
    50                  55                  60

Gly Gly Pro
65

<210> SEQ ID NO 50
<211> LENGTH: 25
<212> TYPE: PRT
<213> ORGANISM: Macaca fascicularis

<400> SEQUENCE: 50

Glu Phe Thr Arg Pro Cys Asp Asp Thr Thr Pro Pro Cys Pro Pro Cys
1               5                   10                  15

Pro Ala Pro Glu Leu Leu Gly Gly Pro
            20                  25

<210> SEQ ID NO 51
<211> LENGTH: 25
<212> TYPE: PRT
<213> ORGANISM: Macaca mulatta

<400> SEQUENCE: 51

Glu Phe Thr Pro Pro Cys Gly Asp Thr Thr Pro Pro Cys Pro Pro Cys
1               5                   10                  15

Pro Ala Pro Glu Leu Leu Gly Gly Pro
            20                  25

<210> SEQ ID NO 52
<211> LENGTH: 20
<212> TYPE: PRT
<213> ORGANISM: Homo sapiens

<400> SEQUENCE: 52

Glu Ser Lys Tyr Gly Pro Pro Cys Pro Ser Cys Pro Ala Pro Glu Phe
1               5                   10                  15

Leu Gly Gly Pro
            20
```

```
<210> SEQ ID NO 53
<211> LENGTH: 18
<212> TYPE: PRT
<213> ORGANISM: Macaca fascicularis

<400> SEQUENCE: 53

Glu Phe Thr Pro Pro Cys Pro Pro Cys Pro Ala Pro Glu Leu Leu Gly
1               5                   10                  15

Gly Pro

<210> SEQ ID NO 54
<211> LENGTH: 18
<212> TYPE: PRT
<213> ORGANISM: Macaca mulatta

<400> SEQUENCE: 54

Glu Phe Thr Pro Pro Cys Pro Pro Cys Pro Ala Pro Glu Leu Leu Gly
1               5                   10                  15

Gly Pro

<210> SEQ ID NO 55
<211> LENGTH: 70
<212> TYPE: PRT
<213> ORGANISM: Homo sapiens

<400> SEQUENCE: 55

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
    50                  55                  60

Glu Leu Leu Gly Gly Pro
65              70

<210> SEQ ID NO 56
<211> LENGTH: 16
<212> TYPE: PRT
<213> ORGANISM: Homo sapiens

<400> SEQUENCE: 56

Thr Cys Pro Pro Cys Pro Ala Pro Glu Leu Leu Gly Gly Pro Ser Val
1               5                   10                  15

<210> SEQ ID NO 57
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Thr Cys Pro Pro Cys Pro Leu Leu Gly Gly Pro Ser Val
1               5                   10

<210> SEQ ID NO 58
<211> LENGTH: 12
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 58

Thr Cys Pro Pro Cys Leu Leu Gly Gly Pro Ser Val
1               5                   10

<210> SEQ ID NO 59
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Cys Pro Pro Cys Pro Ala Pro Pro Val Ala Gly Pro Ser Val
1               5                   10
```

HINGE MODIFIED ANTIBODY FRAGMENTS AND METHODS OF MAKING

CROSS-REFERENCE TO RELATED APPLICATIONS

This application is a continuation of International Patent Application No. PCT/US2016/059137, filed Oct. 27, 2016, which claims priority to U.S. Provisional Patent Application Ser. No. 62/248,792, filed Oct. 30, 2015, and U.S. Provisional Patent Application Ser. No. 62/346,905, filed Jun. 7, 2016, the contents of each of which are incorporated by reference in their entirety, and to each of which priority is claimed.

SEQUENCE LISTING

The instant application contains a Sequence Listing which has been submitted electronically in ASCII format and is hereby incorporated by reference in its entirety. Said ASCII copy, created on Apr. 30, 2018, is named 00B206_0594_SL.txt and is 26,205 bytes in size.

FIELD OF THE INVENTION

The present disclosure relates to antibody fragments (e.g., Fab and F(ab')2) having reduced or no reactivity towards pre-existing anti-hinge antibodies (AHA) and compositions comprising such antibody fragments, as well as methods of making and using such antibody fragments and compositions.

BACKGROUND

Antibodies are composed of two Fab regions that are connected by a flexible hinge-region to the Fc. While the Fab mediates recognition and binding of the antigen, two important functions of the Fc are to mediate effector function by engagement with Fcγ receptors (1) and to confer long serum half-life by binding to the salvage receptor, FcRn (2). In particular, the slow pharmacokinetics of IgG contribute to the success of antibodies as therapeutics as it enables less frequent dosing compared to other biotherapeutics. Consequently, the majority of approved therapeutic antibodies have full-length IgG format. Unlike IgG, the serum half-life of an isolated Fab fragment is short (3) and such property is required for indications when short plasma half-life is desired as with three FDA approved Fab molecules (4). One therapeutic Fab molecule directed against platelet surface receptor GPIIb/IIIa (abciximab, REOPRO®) is commercially produced by proteolytic cleavage with papain (5), which is the original method of Fab production (6). With the advances in molecular cloning, recombinant expression of antibody fragments has become an attractive route to generate Fab molecules as exemplified by the second approved Fab therapeutic, anti-VEGF (ranibizumab, Lucentis®) (7) and the recently approved Fab against dabigatran (idarucizumab, Praxbind®) (33). Fab molecules are advantageous, for example, when transient systemic activity that does not persist past dosing is desired or when administration and activity are localized to a peripheral compartment such as the eye.

Many proteases against the antibody hinge region have been implicated as the mechanism by which pathogens and tumor cells attempt to evade the host immune response (13). Resulting C-terminal neoepitopes, however, are eventually recognized by the immune system and anti-hinge antibodies (AHA) are generated. Such autoantibodies to the upper-hinge region of the Fab and the lower-hinge region of the F(ab')2 have been shown in several studies (17-21). These pre-existing AHA titers vary from donor to donor (20) and it may represent past and current exposure to such neoepitopes. In certain instances, AHA can act as surrogate Fc and restore effector function of proteolytically inactivated antibodies (22). As one rationale for using a Fab or F(ab')2 molecule as the therapeutic format is to eliminate effector function, it would be undesirable to have effector function reinstated by pre-existing AHA and risk any potential safety concerns. Accordingly, there is a need in the art for novel Fab and F(ab')2 molecules that have reduced or no reactivity with pre-existing AHA in human serum to, inter alia, potentially provide a superior safety profile in a therapeutic setting by minimizing immune responses following drug treatment.

SUMMARY

The present disclosure relates to antibody fragments (e.g., Fab and F(ab')2) having reduced or no reactivity towards pre-existing anti-hinge antibodies (AHA) and compositions comprising such antibody fragments, as well as methods of making and using such antibody fragments and compositions.

In certain embodiments, the present disclosure is directed to an isolated antibody fragment and compositions comprising the same, wherein the antibody fragment has reduced or no reactivity towards pre-existing anti-hinge antibodies. In certain embodiments, an isolated antibody fragment of the present disclosure exhibits reduced and/or no binding to FcγRIIIa and/or C1q. In certain embodiments, the antibody fragment is a Fab, Fab' or F(ab')2.

In certain embodiments, the present disclosure is directed to antibody fragments and compositions comprising the same, wherein the antibody fragment is a Fab. In certain embodiments, the present disclosure is directed to Fab molecules wherein the Fab terminates with residue $D_{221}$. In certain embodiments, the Fab terminates with amino acids comprising an amino acid sequence selected from group consisting of CDKTHT (SEQ ID NO: 14), CDKTHL (SEQ ID NO: 15), CDKTH (SEQ ID NO: 16), CDKT (SEQ ID NO: 17), CDK and CD. In certain embodiments, the Fab terminates with amino acids comprising an amino acid sequence selected from group consisting of KYGPP (SEQ ID NO: 18), KYGP (SEQ ID NO: 19), KYG, KY and K. In certain embodiments, the Fab comprises a heavy chain constant region that comprises an amino acid sequence selected from the group consisting of SEQ ID NOs: 1, 2, 3, 4, 5, 6, 7, 8, 9, 10, 11, 12, 13 and conservative modifications of.

In certain embodiments, the present disclosure is directed to an antibody fragment and compositions comprising the same, wherein the antibody fragment is a F(ab')2. In certain embodiments, the present disclosure is directed to F(ab')2 molecules, wherein the F(ab')2 comprises a C-terminal deletion of 1, 2, 3, 4, or 5 amino acids. In certain embodiments of the present disclosure, the F(ab')2 comprises a deletion at position EU231. In certain embodiments of the present disclosure, the F(ab')2 comprises a deletion at positions EU231-232. In certain embodiments of the present disclosure, the F(ab')2 comprises a deletion at positions EU231-233. In certain embodiments of the present disclosure, the F(ab')2 comprises a deletion at position EU231-234. In certain embodiments, the F(ab')2 comprises a deletion at position EU230-234.

In certain embodiments, the present disclosure is directed to an isolated nucleic acid and compositions comprising the same, wherein the nucleic acid encodes an antibody fragment having reduced or no reactivity to AHA. In certain embodiments, the present disclosure is directed to a host cell comprising said nucleic acid. In certain embodiments, the present disclosure is directed to a method of producing an antibody fragment comprising culturing said host cell so that the antibody fragment is produced. In certain embodiments, the present disclosure is directed to a pharmaceutical formulation comprising an antibody fragment having reduced or no reactivity to AHA and a pharmaceutically acceptable carrier.

In certain embodiments, the present disclosure is directed to an antibody fragment having reduced or no reactivity to AHA for use as a medicament. In certain embodiments, the present disclosure is directed to an antibody fragment having reduced or no reactivity to AHA for use in treating a disease. In certain embodiments, the present disclosure is directed to an antibody fragment having reduced or no reactivity to AHA for use in inhibiting or activating a molecular pathway and/or mechanism. In certain embodiments, the present disclosure is directed to the use of an antibody fragment having reduced or no reactivity to AHA in the manufacture of a medicament for the treatment of a disease. In certain embodiments, the present disclosure is directed to the use of an antibody fragment having reduced or no reactivity to AHA in the manufacture of a medicament for inhibiting or activating a molecular pathway and/or mechanism.

In certain embodiments, the present disclosure is directed to methods of treating an individual having a disease comprising administering to the individual an effective amount of an antibody fragment having reduced or no reactivity to AHA. In certain embodiments, the present disclosure is directed to methods of inhibiting or activating a molecular pathway and/or mechanism in an individual comprising administering to the individual an effective amount of an antibody fragment having reduced or no reactivity to AHA to inhibit or activate a molecular pathway and/or mechanism.

BRIEF DESCRIPTION OF THE FIGURES

FIG. 1A discloses SEQ ID NOS 14-15, respectively, in order of appearance. (1B) Pooled human serum was incubated with human IgG1 Fab with different upper hinge lengths and ends. Binding pre-existing antibodies detected by anti-Fc ELISA. Truncating the Fab C-terminus to D221 (D) and the C-terminal variant T225L (DKTHL (SEQ ID NO: 20)) greatly reduced binding of pre-existing antibodies to almost background. Strong response was observed towards T223 as the C-terminal residue (DKT), coinciding with the cleavage site of human neutrophil elastase. The mean value of the individual data points is represented by the horizontal line. FIG. 1B discloses SEQ ID NOS 20-21 and 27, respectively, in order of appearance. (1C) Three different Fabs were incubated with pooled human serum and binding of pre-existing antibodies detected by ELISA. Significant signal was observed for different Fabs with DKTHT (SEQ ID NO: 21) C-terminus. Reduced binding of pre-existing antibodies to the $D_{221}$ and $T_{225}L$ C-terminus was detected across different Fabs. Fab-1 includes the antibody variable domain used in (B) and all other AHA binding experiments throughout Example 1. FIG. 1C discloses SEQ ID NOS 21, 20, 21, 20, 21 and 20, respectively, in order of appearance. (1D) Pooled human serum was incubated with human IgG2 Fab and IgG4 Fabs with different upper hinge length and binding antibodies detected by ELISA. No pre-existing antibodies can be detected to the upper hinge of human IgG2 and IgG4. FIG. 1D discloses SEQ ID NO: 18.

FIGS. 2A-2C show the cleavage of IgG1-2 chimera by IdeS. (2A) Model of the F(ab')$_2$ region of antibody cAC10 modeled with MOE; light chain (201), heavy chain (202), interchain disulfide (203), and lower hinge (204). The P1 position of IdeS is G236. Numbering of residues is according to EU numbering nomenclature. FIG. 2A discloses SEQ ID NO: 30. (2B) Alignment of the lower hinge of IgG1 and the IgG1-2 chimera. Residues in cyan are IgG2 isotype residues introduced into the lower hinge of IgG2. FIG. 2B discloses SEQ ID NOS 31 and 59, respectively, in order of appearance. (2C) Cleavage efficiency of human IgG1 and IgG1-2 chimera. 1 mg/ml of IgG1 and IgG1-2 were incubated for 24 hours at 37° C. with different IdeS amounts as indicated. Cleavage was analyzed by capillary electrophoresis. While IgG1 was efficiently cleaved into F(ab')$_2$ at an IdeS:IgG ratio of 1:500, IgG1-2 requires 50-fold higher IdeS concentrations for complete cleavage.

FIG. 3D discloses SEQ ID NOS 31-34, respectively, in order of appearance. (3E) Cleavage efficiency of the 76 human IgG1 variants with IdeS. FIG. 3E discloses SEQ ID NO: 31.

FIGS. 4A-4B show the reactivity of P1 and P2 variants towards pre-existing AHA. (4A) IdeS is efficiently removed during purification and cannot be detected in the purified F(ab')$_2$ variants by SDS-PAGE followed by coomassie staining (upper panel) or immunoblot analysis with anti-IdeS antibodies (lower panel). (4B) Pooled human serum was incubated with human IgG1 Fab with T225 C-terminus and F(ab')$_2$ generated by IdeS cleavage of antibodies with variants in P1 and P2 positions. Binding pre-existing antibodies were detected by ELISA. The F(ab')$_2$ showed a signal that was about 1.7 fold higher compared to the Fab. The hinge variants reduced reactivity to levels comparable to Fab but did not eliminate reactivity completely.

While deletion of the IdeS P3 residue (L234) in the lower hinge severely impacted cleavage efficiency, deletion of the P4 (E233) or P5 (P232) positions did not impact cleavage with IdeS compared to wild-type (WT). (5B) Deletion of the P4 and P5 positions was not sufficient to avoid binding of pre-existing AHA. (5C) IdeS cleavage of antibodies with deletions of the IdeS P4 through P6 (ΔP456) and P4 through P7 (ΔP4567) sites. While cleavage efficiency of the ΔP4567 variant was slightly reduced compared to the wild-type lower hinge sequence (WT), ΔP456 displayed cleavage efficiency comparable to the wild-type at IdeS:IgG ratio of 1:200. (5D) Pooled human serum was incubated with F(ab')$_2$ produced by IdeS digestion and binding antibodies detected by ELISA. Lower hinge deletions ΔP456 and ΔP4567 were not recognized by pre-existing AHA. (5E) IdeS cleaved the ΔP456 hinge variant with high specificity. After digestion of wild-type (WT) and ΔP456 hinge IgG, reduced F(ab')$_2$ was analyzed by mass spectrometry. Only a single heavy chain species corresponding to the expected molecular mass was observed. (5F) Schematic diagram depicting the deletions generated in the lower hinge region. FIG. 5F discloses SEQ ID NOS 35, 31, 36-40, 31, and 41-42, respectively, in order of appearance.

FIG. 6A discloses SEQ ID NOS 43-54, respectively, in order of appearance. FIG. 6B discloses SEQ ID NOS 43, 46, 55 and 52, respectively, in order of appearance.

FIGS. 9A-9D show the reactivity of deletion variants with modified P1 and P2 residues with pre-existing AHA. (9A) The cleavage efficiency of the variants was assessed by amount of F(ab')$_2$ produced at an IdeS:IgG ratio of 1:10. FIG. 9A discloses SEQ ID NO: 31. (9B) The cleavage efficiency of the variants was assessed by the amount of F(ab')$_2$ produced at an IdeS:IgG ratio of 1:100. FIG. 9B discloses SEQ ID NO: 31. (9C) The cleavage efficiency of the variants was assessed by amount of F(ab')$_2$ produced at an IdeS:IgG ratio of 1:500. FIG. 9C discloses SEQ ID NO: 31. (9D) Detection of the bound pre-existing AHA to the variants by anti-Fc ELISA. FIG. 9D discloses SEQ ID NO: 56.

FIG. 10A discloses SEQ ID NOS 56-57, respectively, in order of appearance. (10B) Detection of pre-existing AHA bound to the variants by anti-Fc ELISA. FIG. 10B discloses SEQ ID NO: 56.

DETAILED DESCRIPTION

I. Definitions

Figure 1A:
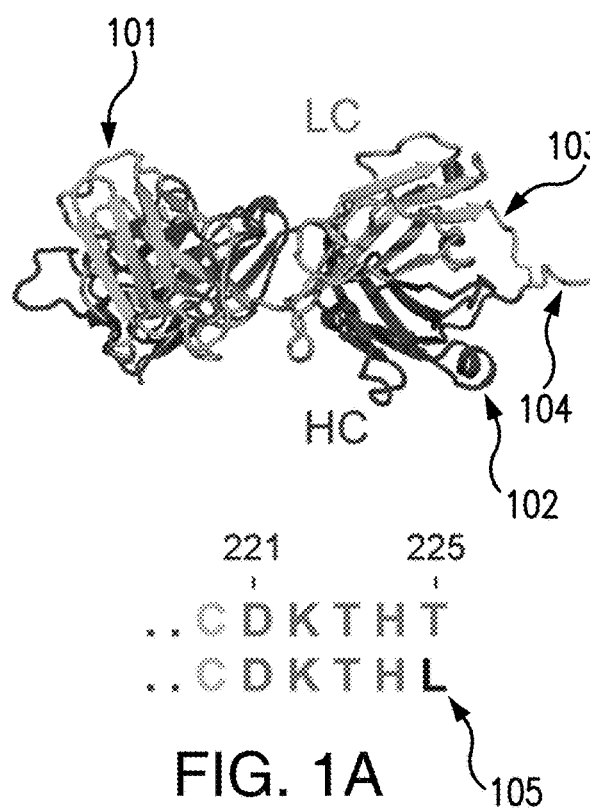
FIGS. 1A-1D show the binding of pre-existing human antibodies to the Fab of human IgG1, IgG2 and IgG4. (1A) X-ray crystal structure of the Fab region (PDB: 1HZH) including the upper hinge; light chain (101), heavy chain (102), interchain disulfide (103), and upper hinge (104). In the isolated Fab molecule the upper hinge is a protruding unstructured region without structural and functional role. The residues of the upper hinge are displayed in magenta to indicate the T225L mutation (105) that is perturbing binding to pre-existing AHA. Numbering of residues is according to EU numbering nomenclature.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments. In certain embodiments, the antibody fragment is a Fab molecule. In certain embodiments, the antibody fragment is a F(ab')$_2$ molecule.

The terms "full length antibody," "intact antibody," and "whole antibody" are used herein interchangeably to refer to an antibody having a structure substantially similar to a native antibody structure or having heavy chains that contain an Fc region as defined herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains ($C_H1$, $C_H2$, and $C_H3$). Similarly, from N- to C-terminus, each light chain has a variable region (VL), also called a variable light domain or a light chain variable domain, followed by a constant light (CL) domain. The light chain of an antibody can be assigned to one of two types, called kappa (κ) and lambda (λ), based on the amino acid sequence of its constant domain.

The term "Fc region" herein is used to define a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Fc receptor" or "FcR" describes a receptor that binds to the Fc region of an antibody. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see, e.g., Daëron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward., *Immunol. Today* 18(12):592-598 (1997); Ghetie et al., *Nature Biotechnology*, 15(7):637-640 (1997); Hinton et al., *J. Biol. Chem.* 279(8):6213-6216 (2004); WO 2004/92219 (Hinton et al.).

Binding to human FcRn in vivo and serum half-life of human FcRn high affinity binding polypeptides can be assayed, e.g., in transgenic mice or transfected human cell lines expressing human FcRn, or in primates to which the polypeptides with a variant Fc region are administered. WO 2000/042072 (Presta) describes antibody variants with improved or diminished binding to FcRs. See also, e.g., Shields et al. *J. Biol. Chem.* 9(2):6591-6604 (2001).

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The "hinge region" is generally defined as stretching from 216-238 (EU numbering) or 226-251 (Kabat numbering) of human IgG1. The hinge can be further divided into three distinct regions, the upper, middle (e.g., core) and lower hinge. See, e.g., Brerski and Georgiou, Curr. Opin. Immunol. 40, 62-69 (2016), which is incorporated by reference herein in its entirety. In certain embodiments, the hinge region of a human IgG1 antibody is generally defined as follows:

The upper hinge comprises amino acids having the sequence EPKSCDKTHT (SEQ ID NO: 22). In certain embodiments, the upper hinge comprises the amino acids at positions 216-225 (EU numbering) or 226-238 (Kabat numbering).

The middle (e.g., core) hinge comprises amino acids having the sequence CPPC (SEQ ID NO: 23). In certain embodiments, the core hinge comprises the amino acids at positions 226-229 (EU numbering) or 239-242 (Kabat numbering).

The lower hinge comprises amino acids having the sequence PAPELLGGP (SEQ ID NO: 24). In certain embodiments, the lower hinge comprises the amino acids at positions 230-238 (EU numbering) or 243-251 (Kabat numbering).

The "class" of an antibody refers to the type of constant domain or constant region possessed by its heavy chain. There are five major classes of antibodies: IgA, IgD, IgE, IgG, and IgM, and several of these can be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$, respectively.

An "isolated" antibody or antibody fragment is one which has been separated from a component of its natural environment. An antibody or an antibody fragment can be purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or can be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny can be completely identical in nucleic acid content to a parent cell, or can contain mutations. Mutant progeny that have the same function or biological activity as screened or selected for in the originally transformed cell are included herein.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In certain embodiments, antibody fragments of the present disclosure are used to delay development of a disease or to slow the progression of a disease.

An "effective amount" of an agent, e.g., an antibody fragment disclosed herein, or a pharmaceutical formulation comprising an agent, refers to an amount effective, at dosages and for periods of time necessary, to achieve the desired therapeutic or prophylactic result.

The term "package insert" is used to refer to instructions customarily included in commercial packages of therapeutic products, that contain information about the indications, usage, dosage, administration, combination therapy, contraindications and/or warnings concerning the use of such therapeutic products.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

II. Compositions and Methods

In certain embodiments, the present disclosure is based, in part, on methods of engineering antibody fragments to evade pre-existing anti-hinge antibodies (AHA). In certain embodiments, antibody fragments (e.g., Fab and F(ab')$_2$) that have reduced or no reactivity towards AHA and methods of making these antibody fragments are provided. In certain embodiments, antibody fragments of the present disclosure can provide superior safety in a therapeutic setting by minimizing immune response following drug treatments.

A. Exemplary Antibody Fragments

In certain embodiments, the present disclosure provides antibody fragments (e.g., Fab, Fab' and F(ab')$_2$), and compositions comprising the same, that have reduced or no reactivity towards AHA. For example, but not by way of limitation, an antibody fragment disclosed herein exhibits AHA reactivity that is reduced by at least 10%, at least 20%, at least 30%, at least 40%, at least 50%, at least 60%, at least 70%, at least 80%, at least 90% or at least 100% relative to a reference antibody fragment, e.g., an antibody fragment with a native hinge region. In certain embodiments, the reference antibody fragment is an IgG1 antibody fragment that has a native hinge region.

In certain embodiments, the isolated antibody fragments of the present disclosure, and the compositions comprising the same, exhibit reduced and/or no binding to FcγRIIIa and/or C1q. For example, and not by way of limitation, an antibody fragment of the present disclosure exhibits binding to FcγRIIIa and/or C1q that is reduced by at least 10%, at least 20%, at least 30%, at least 40%, at least 50%, at least 60%, at least 70%, at least 80%, at least 90% or at least 100% relative to a reference antibody fragment, e.g., an antibody fragment with a native hinge region. In certain embodiments, the reference antibody fragment is an IgG1 antibody fragment that has a native hinge region.

In certain embodiments, an antibody fragment employed in the context of the methods described herein comprises a native hinge region or a modified hinge region. For example, and not by way of limitation, an antibody fragment of the present disclosure can be a Fab fragment that comprises a native hinge region or modified hinge region. In certain embodiments, the antibody fragment of the present disclosure is a F(ab)$_2$ that comprises a native hinge region or modified hinge region.

A native hinge region is a hinge region normally associated with the $C_H1$ domain of an antibody molecule. In certain embodiments, the native hinge region of a presently disclosed antibody fragment can be of the IgG1, IgG2, IgG3 or IgG4 isotype. For example, and not by way of limitation, the Fab fragment can be of the IgG1, IgG2, IgG3 or IgG4 isotype. In certain embodiments, the antibody fragment, e.g., the Fab fragment, is of the IgG2 isotype comprising a native hinge region. In certain embodiments, the antibody fragment, e.g., the Fab fragment, is of the IgG4 isotype comprising a native hinge region.

A modified hinge region is any hinge that differs in length and/or composition from the native hinge region. Such hinges can include hinge regions from other species, such as human, mouse, rat, rabbit, pig, hamster, camel, llama or goat hinge regions. Other modified hinge regions can comprise a complete hinge region derived from an antibody of a different class or subclass from that of the $C_H1$ domain. Thus, for instance, a $C_H1$ domain of class γ1 can be attached to a hinge region of class γ4. Alternatively, the modified hinge region can comprise part of a natural hinge or a repeating unit in which each unit in the repeat is derived from a natural hinge region.

In certain embodiments, the native hinge region is altered by substituting, deleting and/or adding one or more amino acid residues to generate a modified hinge region. In certain embodiments, the Fab fragment is of the IgG1 isotype comprising a modified hinge region. In certain embodiments, the Fab fragment is of the IgG2 isotype comprising a modified hinge region. In certain embodiments, the Fab fragment is of the IgG4 isotype comprising a modified hinge region.

In certain embodiments, a modified hinge region comprises the substitution, deletion and/or addition of one or more amino acids within the upper hinge region. For example, and not by way of limitation, a modified hinge region of the disclosed subject matter can have one or more substitutions, deletions and/or additions at amino acid positions EU216-225. Alternatively or additionally, a modified hinge region comprises the substitution, deletion and/or addition of one or more amino acids within the lower hinge region. In certain embodiments, a modified hinge region of the disclosed subject matter can have one or more substitutions, deletions and/or additions at amino acid positions EU230-238. Alternatively or additionally, a modified hinge region can comprise the addition of one or more amino acids C-terminal to amino acid position EU238. In certain embodiments, a modified hinge region comprises the substitution, deletion and/or addition of one or more amino acids within the middle, e.g., core, hinge region. For example, and not by way of limitation, a modified hinge region of the disclosed subject matter can have one or more substitutions, deletions and/or additions at amino acid positions EU226-229.

In certain embodiments, the modification or alteration is a substitution of one or more, two or more, three or more, four or more, five or more or six or more amino acid residues. In certain embodiments, the substitution can be generated within the upper hinge region, middle hinge region and/or the lower hinge region. In certain embodiments, the amino acid residue at position 225 can be substituted. For example, and not by way of limitation, the amino acid residue at position 225 can be changed to any amino acid except for threonine (T). In certain embodiments, the amino acid at position 225, e.g., threonine, can be changed to a leucine (L), e.g., T225L, according to EU numbering. In certain embodiments, an antibody fragment of the present disclosure is a Fab fragment comprising the substitution T225L.

Figure 6A:
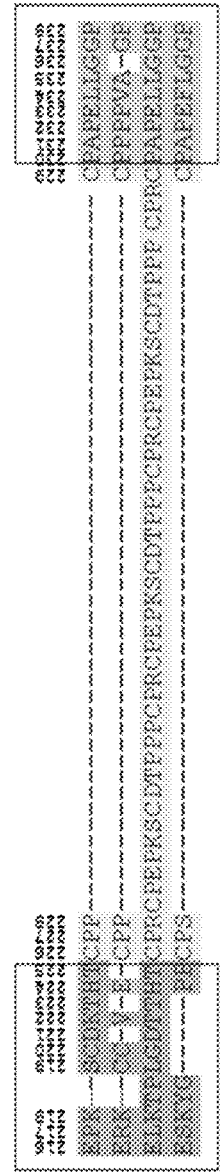
FIGS. 6A-6B show the alignment of the amino acid residues (6A) and EU numbering of the amino acid residues (6B) within the upper, core and lower hinge regions of the IgG1, IgG2, IgG3 and IgG4 isotypes in human, cynomolgus monkey and rhesus monkey.
Figure 6B:

In certain embodiments, the upper hinge region of an IgG1 antibody fragment can be substituted with one or more amino acids residues present within the upper hinge region of an IgG2 and/or an IgG4 antibody because, for example, the upper hinge regions of IgG2 and IgG4 antibodies exhibit reduced or no reactivity towards AHA (see, e.g., FIG. 1). For example, and not by way of limitation, the upper hinge region of an IgG1 antibody fragment can be substituted with one or more amino acids residues present within the native hinge region of an IgG2 and/or an IgG4 antibody (see FIG. 6). In certain embodiments, a modified hinge region of an IgG1 antibody fragment retains a cysteine at amino acid position EU220 (e.g., as compared to the native hinge region of an IgG1 antibody). In certain embodiments, a modified hinge region of an IgG1 antibody fragment does not retain a cysteine at amino acid position EU220, e.g., in an IgG antibody fragment where the upper hinge region of the IgG1 antibody fragment is replaced with the upper hinge region (e.g., entire upper hinge region) of IgG4. In certain embodiments, the upper hinge region of an IgG1 antibody fragment can be substituted with one or more amino acids residues present within the upper hinge region of an IgG2, IgG3 and/or an IgG4 antibody, where the amino acid residue at position 131 of the IgG1 antibody is changed from a serine (S) to a cysteine (C), i.e., S131C.

In certain embodiments, an antibody fragment of the present disclosure, e.g., a Fab, F(ab')$_2$ or Fab', can comprise a substitution at amino acid positions EU235-236. For example, and not by way of limitation, the amino acid at position 236, e.g., glycine (G), can be changed to an alanine (A), e.g., G236A. In certain embodiments, an antibody fragment, e.g., a F(ab')$_2$, can comprise a substitution at position 235, according to EU numbering. In certain embodiments, the amino acid at position 235, e.g., leucine (L), can be changed to a valine (V), e.g., L235V, changed to an isoleucine (I) e.g., L235I, or changed to a methionine (M) e.g., L235M.

In certain embodiments, the modification or alteration is a deletion of one or more, two or more, three or more, four or more, five or more or six or more amino acid residues. In certain embodiments, the one or more deletions can be generated within the upper hinge region, middle hinge region and/or the lower hinge region. In certain embodiments, an antibody fragment of the present disclosure, e.g., a Fab, F(ab')$_2$ or Fab', comprises a modified hinge region that has one or more deletions of one or more amino acids at positions EU230-238. In certain embodiments, the antibody fragment comprises a deletion at position EU231. In certain embodiments, the antibody fragment comprises a deletion at positions EU231 and EU232. In certain embodiments, the antibody fragment comprises deletions at positions EU231, EU232 and EU233. In certain embodiments, the antibody fragment comprises deletions at positions EU231, EU232, EU233 and EU234. In certain embodiments, the antibody fragment comprises deletions at positions EU230, EU231, EU232, EU233 and EU234.

In certain embodiments, an antibody fragment of the present disclosure comprises a C-terminal deletion of one or more, two or more, three or more, four or more, five or more or six or more amino acids. In certain embodiments, an antibody fragment of the present comprises the deletion of one or more amino acids in the upper hinge region, e.g., to generate a C-terminal truncation. In certain embodiments, one or more amino acid at positions EU222-225 can be deleted to obtain a C-terminal truncation. In certain embodiments, an antibody fragment disclosed herein, e.g., a Fab fragment, comprises a C-terminal truncation. For example, and not by way of limitation, the C-terminus of an antibody fragment disclosed herein, e.g., a Fab fragment, terminates at amino acid residue D221 (according to EU numbering). In certain embodiments, the C-terminus of an antibody fragment disclosed herein, e.g., a Fab fragment, terminates at amino acid residue K222 (according to EU numbering).

In certain embodiments, the C-terminus of the heavy chain of an antibody fragment, e.g., a Fab fragment, disclosed herein, terminates with amino acids having a sequence selected from CDKTHT (SEQ ID NO: 14), CDKTHL (SEQ ID NO: 15), CDKTH (SEQ ID NO: 16), CDKT (SEQ ID NO: 17), CDK and CD. In certain embodiments, the C-terminus of the heavy chain of the Fab fragment terminates in the amino acid sequence CDKTHX (SEQ ID NO: 25), wherein X is any amino acid except T. In certain embodiments, a Fab fragment comprises a heavy chain constant region selected from "CDKTHT," (SEQ ID NO: 14) "CDKTHL," (SEQ ID NO: 15) "CDKTH," (SEQ ID NO: 16) "CDKT," (SEQ ID NO: 17) "CDK" or "CD," as disclosed in Table 1. In certain embodiments, the presently disclosed subject matter provides antibody fragments, e.g., Fab fragment, that comprise a heavy chain constant region that comprises an amino acid sequence as set forth in SEQ ID NOs: 1, 2, 3, 4, 5 or 6. In certain embodiments, an antibody fragment of the present disclosure comprises a heavy chain constant region that comprises the amino acid sequence set forth in SEQ ID NO:5. In certain embodiments, an antibody fragment of the present disclosure comprises a heavy chain constant region that comprises the amino acid sequence set forth in SEQ ID NO:6.

In certain embodiments, as an alternative to truncation and/or mutation at the C-terminus, to avoid pre-existing AHA responses, IgG2 or IgG4 Fab fragments can be used. For example, and not by way of limitation, an antibody fragment of the present disclosure can comprise a heavy chain constant region that comprises the amino acid sequence in SEQ ID NOs: 7 or 8. In certain embodiments, an IgG2 or IgG4 Fab fragment can comprise a C-terminal deletion of one or more, two or more, three or more, four or more or five or more amino acids. In certain embodiments, a Fab of the present disclosure is an IgG2 Fab fragment comprising a heavy chain constant region ending in the sequence VERK (SEQ ID NO: 26). In certain embodiments, the C-terminus of the heavy chain of an antibody fragment, e.g., an IgG4 Fab fragment, disclosed herein, terminates with amino acids having a sequence selected from KYGPP (SEQ ID NO: 18), KYGP (SEQ ID NO: 19), KYG, KY and K. In certain embodiments, a Fab of the present disclosure is an IgG4 Fab fragment comprising a heavy chain constant region selected from "KYGPP," (SEQ ID NO: 18) "KYGP," (SEQ ID NO: 19) "KYG," "KY" and "K," as disclosed in Table 1. For example, and not by way of limitation, an antibody fragment of the present disclosure can comprise a heavy chain constant region that comprises the amino acid sequence set forth in SEQ ID NOs: 9, 10, 11, 12 or 13.

TABLE 1

| Fab Heavy Chain Sequences | |
|---|---|
| Fab heavy chain constant region "CDKTHT" (SEQ ID NO: 14) | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THT (SEQ ID NO: 1) |
| Fab heavy chain constant region "CDKTHL" (SEQ ID NO: 15) | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK THL (SEQ ID NO: 2) |
| Fab heavy chain constant region "CDKTH" (SEQ ID NO: 16) | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK TH (SEQ ID NO: 3) |
| Fab heavy chain constant region "CDKT" (SEQ ID NO: 17) | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK T (SEQ ID NO: 4) |
| Fab heavy chain constant region "CDK") | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCDK (SEQ ID NO: 5) |
| Fab heavy chain constant region "CD" | ASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KKVEPKSCD (SEQ ID NO: 6) |
| Fab heavy chain constant region IgG2 | ASTKG PSVFPLAPCS RSTSESTAAL GCLVKDYFPE PVTVSWNSGA LTSGVHTFPA VLQSSGLYSL SSVVTVPSSN FGTQTYTCNV DHKPSNTKVD KTVERK (SEQ ID NO: 7) |
| Fab heavy chain constant region IgG4 | ASTKG PSVFPLAPCS RSTSESTAAL GCLVKDYFPE PVTVSWNSGA LTSGVHTFPA VLQSSGLYSL SSVVTVPSSS LGTKTYTCNV DHKPSNTKVD KRVESKYGPP (SEQ ID NO: 8) |

TABLE 1-continued

Fab Heavy Chain Sequences

| | |
|---|---|
| Fab heavy chain constant region IgG4 ("KYG") | ASTKG PSVFPLAPCS RSTSESTAAL GCLVKDYFPE PVTVSWNSGA LTSGVHTFPA VLQSSGLYSL SSVVTVPSSS LGTKTYTCNV DHKPSNTKVD KRVESKYG (SEQ ID NO: 9) |
| Fab heavy chain constant region IgG4 ("KYGP") (SEQ ID NO: 19) | ASTKG PSVFPLAPCS RSTSESTAAL GCLVKDYFPE PVTVSWNSGA LTSGVHTFPA VLQSSGLYSL SSVVTVPSSS LGTKTYTCNV DHKPSNTKVD KRVESKYGP (SEQ ID NO: 10) |
| Fab heavy chain constant region IgG4 ("KYGPP") (SEQ ID NO: 18) | ASTKG PSVFPLAPCS RSTSESTAAL GCLVKDYFPE PVTVSWNSGA LTSGVHTFPA VLQSSGLYSL SSVVTVPSSS LGTKTYTCNV DHKPSNTKVD KRVESKYGPP (SEQ ID NO: 11) |
| Fab heavy chain constant region IgG4 ("KY") | ASTKG PSVFPLAPCS RSTSESTAAL GCLVKDYFPE PVTVSWNSGA LTSGVHTFPA VLQSSGLYSL SSVVTVPSSS LGTKTYTCNV DHKPSNTKVD KRVESKY (SEQ ID NO: 12) |
| Fab heavy chain constant region IgG4 ("K") | ASTKG PSVFPLAPCS RSTSESTAAL GCLVKDYFPE PVTVSWNSGA LTSGVHTFPA VLQSSGLYSL SSVVTVPSSS LGTKTYTCNV DHKPSNTKVD KRVESK (SEQ ID NO: 13) |

The present disclosure further provides antibody fragments that comprise conservative modifications of the sequences disclosed herein. For example, and not by way of limitation, the present disclosure provides antibody fragments that comprise a heavy chain constant region that comprises an amino acid sequence set forth in SEQ ID NOs: 1, 2, 3, 4, 5, 6, 7, 8, 9, 10, 11, 12, 13 or conservative modifications thereof, and wherein the antibody fragment retains the desired properties of the antibody fragments disclosed herein. For example, and not by way of limitation, such antibody fragments have reduced or no reactivity towards AHA, as disclosed above.

As used herein, the term "conservative sequence modification" is intended to refer to amino acid modifications that do not significantly affect characteristics of the antibody fragment containing the amino acid sequence. Such conservative modifications include amino acid substitutions, additions and deletions. Modifications can be introduced into an antibody fragment of the present disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. Exemplary conservative amino acid substitutions are shown in Table 2.

In certain embodiments, a sequence disclosed herein can have up to about one, up to about two, up to about three, up to about four, up to about five, up to about six, up to about seven, up to about eight, up to about nine or up to about ten amino acid residues that are modified and/or substituted.

Amino acids can be grouped according to common side-chain properties:
  i. hydrophobic: Norleucine, Met, Ala, Val, Leu, Ile;
  ii. neutral hydrophilic: Cys, Ser, Thr, Asn, Gln;
  iii. acidic: Asp, Glu;
  iv. basic: His, Lys, Arg;
  v. residues that influence chain orientation: Gly, Pro;
  vi. aromatic: Trp, Tyr, Phe.

In certain embodiments, non-conservative substitutions can entail exchanging a member of one of these classes for another class.

TABLE 2

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Other modified hinge regions of the present disclosure can be entirely synthetic and can be designed to possess desired properties such as length, composition and flexibility. For example, and not by way of limitation, a modified hinge region of the present disclosure can be altered to increase or decrease the flexibility of the hinge region. For example, and not by way of limitation, modifications which can increase the flexibility of the hinge region include, but are not limited to, the substitution of one or more amino acids residues with one or more amino acid residues which increase the flexibility (e.g., glycine). In certain embodiments, modifications which can decrease the flexibility of the hinge region include, but are not limited to, the substitution of one or more amino acids residues with one or more amino acid residues which crease the rigidity of the polypeptide (e.g., proline).

B. Methods of Making Antibody Fragments

In certain embodiments, the antibody fragments are made by hinge engineering technology.

In certain embodiments, the antibody fragment starting material for use in connection with the methods described herein can be obtained from any whole antibody (e.g., a whole monoclonal antibody), using any suitable enzymatic cleavage and/or digestion techniques. In certain embodiments, the antibody fragment can be obtained by cleavage with IdeS.

In certain embodiments, Fab molecules are generated by proteolytic digestion or recombinant expression. Proteolytic digestion was the original method of Fab production (6). Generating Fab molecules via proteolytic digestion results in the C-terminal sequence of the Fab heavy chain defined by the protease cleavage site. In turn, a Fab molecule typically includes a portion of the upper hinge of the antibody. This upper hinge region of the antibody serves as the linker between Fab and Fc region but has no structural or functional role in a Fab molecule. It can be considered as an unstructured appendix (see FIG. 1A) as it is often not fully resolved in crystal structures of Fab molecules. One therapeutic Fab molecule directed against platelet surface receptor GPIIb/IIIa (abciximab, REOPRO®) is commercially produced by proteolytic cleavage.

With the advances in molecular cloning, recombinant expression of antibody fragments is an attractive route to generate Fab molecules (7). In contrast to proteolytic digestion as a production route, the recombinant expression of Fab molecules provides flexibility in defining the length of the included upper hinge region. In certain embodiments, the Fab fragments are produced by recombinant expression.

The high affinity of an antibody is often enabled by bivalent target engagement, facilitating avidity. In contrast, the target engagement of a Fab is monovalent. This often leads to lower target affinity compared to the full-length IgG. By joining two Fab fragments to create a F(ab')$_2$, avidity can be restored while preserving key properties of the Fab, such as short serum half-life. In addition, targeting multiple disease mediators by bispecific antibodies has become increasingly important for therapeutic antibody development (8). F(ab')$_2$ molecules can provide a natural scaffold to produce small bispecific antibody fragments. In contrast to the production of Fab molecules, the recombinant expression of F(ab')$_2$ is not naturally possible because expressed Fab' molecules require non-native homo- or heterodimerization domains as a fusion (9, 10). Hence, there are two main approaches to generate F(ab')$_2$ molecules: (i) chemical conjugation and (ii) proteolytic digestion. For chemical conjugation, recombinantly generated Fab' molecules are coupled by homo- or heterobifunctional crosslinkers (3, 9, 11, 12). Analogous to the proteolytic digestion approach to produce Fab molecules, a number of known proteases can cleave the intact antibody in the lower hinge region to produce F(ab')$_2$ molecules (13). Such proteolytic digestion results in very stable F(ab')$_2$ molecules where the two Fab molecules are connected by the two disulfide-bonds of the core-hinge. Pepsin is most widely used (14) but a highly specific IgG degrading enzyme of *Streptococcus pyogenes*, IdeS, has been described more recently (15, 16). The use of IdeS enables generation of highly homogenous product by eliminating the C-terminal heterogeneity observed from pepsin digest (3). In certain embodiments, the F(ab')$_2$ fragments are produced by IdeS cleavage.

C. Recombinant Methods and Compositions

Antibody fragments can be produced using recombinant methods and compositions, e.g., as described in U.S. Pat. No. 4,816,567. In certain embodiments, an isolated nucleic acid encoding an antibody fragment described herein or composition comprising such nucleic acid is provided. In addition, one or more vectors (e.g., expression vectors) comprising such nucleic acid are provided. A host cell comprising such nucleic acid is also provided. In certain embodiments, the host cell is eukaryotic, e.g. a Chinese Hamster Ovary (CHO) cell or lymphoid cell (e.g., Y0, NS0, Sp20 cell). In certain embodiments, a method of making a Fab molecule is provided, wherein the method comprises culturing a host cell comprising a nucleic acid encoding the Fab, as provided above, under conditions suitable for expression of the Fab, and optionally recovering the Fab from the host cell (or host cell culture medium).

For recombinant production of a Fab, a nucleic acid encoding a Fab, e.g., as described above, is isolated and inserted into one or more vectors for further cloning and/or expression in a host cell. Such nucleic acid can be readily isolated and sequenced using conventional procedures (e.g., by using oligonucleotide probes that are capable of binding specifically to genes encoding the heavy and light chains of the Fab).

Suitable host cells for cloning or expression of Fab-encoding vectors include prokaryotic or eukaryotic cells described herein. For example, Fabs can be produced in bacteria. For expression of antibody fragments, such as Fabs, in bacteria, see, e.g., U.S. Pat. Nos. 5,648,237, 5,789, 199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the Fab can be isolated from the bacterial cell paste in a soluble fraction and can be further purified.

In addition to prokaryotes, eukaryotic microbes such as filamentous fungi or yeast are suitable cloning or expression hosts for Fab-encoding vectors, including fungi and yeast strains whose glycosylation pathways have been "humanized." See Gerngross, *Nat. Biotech.* 22:1409-1414 (2004), and Li et al., *Nat. Biotech.* 24:210-215 (2006).

Suitable host cells for the expression of glycosylated proteins are also derived from multicellular organisms (invertebrates and vertebrates). Examples of invertebrate cells include plant and insect cells. Numerous baculoviral strains have been identified which can be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells can also be used as hosts. For example, mammalian cell lines that are adapted to grow in suspension can be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al.,

*Proc. Natl. Acad. Sci. USA* 77:4216 (1980)); and myeloma cell lines such as Y0, NS0 and Sp2/0. For a review of certain mammalian host cell lines suitable for Fab production, see, e.g., Yazaki and Wu, *Methods in Molecular Biology, Vol.* 248 (B. K. C. Lo, ed., Humana Press, Totowa, N.J.), pp. 255-268 (2003).

D. Pharmaceutical Formulations

Pharmaceutical formulations of an antibody fragments, e.g., Fab and F(ab')$_2$, as described herein, are prepared by mixing such antibody fragment having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. For example, but not by way of limitation, lyophilized antibody formulations are described in U.S. Pat. No. 6,267,958. In certain embodiments, aqueous antibody formulations can include those described in U.S. Pat. No. 6,171,586 and WO2006/044908, the latter formulations including a histidine-acetate buffer.

In certain embodiments, an antibody fragment of the present disclosure can be of a purity greater than about 80%, greater than about 90%, greater than about 91%, greater than about 92%, greater than about 93%, greater than about 94%, greater than about 95%, greater than about 96%, greater than about 97%, greater than about 98%, greater than about 99%, greater than about 99.1%, greater than about 99.2%, greater than about 99.3%, greater than about 99.4%, greater than about 99.5%, greater than about 99.6%, greater than about 99.7%, greater than about 99.8% or greater than about 99.9%.

Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

The formulation herein can also contain more than one active ingredients as necessary for the particular indication being treated, preferably those with complementary activities that do not adversely affect each other. Such active ingredients are suitably present in combination in amounts that are effective for the purpose intended.

A composition of the present disclosure can be administered by a variety of methods known in the art. The route and/or mode of administration vary depending upon the desired results. The active compounds can be prepared with carriers that protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are described by e.g., Sustained and Controlled Release Drug Delivery Systems, J. R. Robinson, ed., Marcel Dekker, Inc., New York, 1978. In certain embodiments, the pharmaceutical compositions are manufactured under Good Manufacturing Practice (GMP) conditions of the U.S. Food and Drug Administration.

The carrier can be suitable for intravenous, intramuscular, subcutaneous, parenteral, spinal or epidermal administration (e.g., by injection or infusion). Depending on the route of administration, the active compound, i.e., antibody fragment, can be coated in a material to protect the compound from the action of acids and other natural conditions that can inactivate the compound.

Active ingredients can be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations can be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility can be readily accomplished, e.g., by filtration through sterile filtration membranes.

The disclosed pharmaceutical compositions can also contain adjuvants such as preservatives, wetting agents, emulsifying agents and dispersing agents. Prevention of presence of microorganisms can be ensured both by sterilization procedures, supra, and by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

In certain embodiments, when the antibodies of the present invention are administered as pharmaceuticals, to humans and animals, they can be given alone or as a pharmaceutical composition containing, for example, from about 0.01% to about 99.5% (or about 0.1 to about 90%) of an antibody fragment in combination with a pharmaceutically acceptable carrier.

E. Therapeutic Methods and Compositions

Any of the antibody fragments provided herein can be used in therapeutic methods. In certain embodiments, an antibody fragment for use as a medicament is provided. In certain embodiments, an antibody fragment for use in treating a particular disease indication is provided. In certain embodiments, an antibody fragment of the present disclosure can be used treat an ocular disease and/or disorder. In certain embodiments, an antibody fragment of the present disclosure can be used treat a disease and/or a disorder that would benefit from the application of an antibody fragment that exhibits a short systemic half-life. In certain embodiments, an antibody fragment for use in a method of treatment is provided.

In certain embodiments, the present disclosure provides an antibody fragment for use in a method of treating an individual having a specific disease comprising administering to the individual an effective amount of the antibody fragment or compositions comprising the same. In certain embodiments, the method further comprises administering to the individual an effective amount of at least one additional therapeutic agent, e.g., as described below. In certain embodiments, the present disclosure provides an antibody fragment for use in inhibiting a particular molecular pathway and/or mechanism. In certain embodiments, the present disclosure provides an antibody fragment for use in a method of inhibiting a particular molecular pathway and/or mechanism in an individual that comprises administering to the individual an effective of the antibody fragment to inhibit the particular molecular pathway and/or mechanism. In certain embodiments, the present disclosure provides an antibody fragment for use in activating a particular molecular pathway and/or mechanism. In certain embodiments, the present disclosure provides an antibody fragment for use in a method of activating a particular molecular pathway and/or mechanism in an individual that comprises administering to the individual an effective of the antibody fragment to inhibit the particular molecular pathway and/or mechanism. An "individual" according to any of the above embodiments can be a human.

In certain embodiments, the present disclosure provides for the use of an antibody fragment in the manufacture or preparation of a medicament. In certain embodiments, the medicament is for treatment of a particular disease. In certain embodiments, the medicament is for use in a method of treating a particular disease comprising administering to an individual having the disease an effective amount of the medicament. In certain embodiments, the method further comprises administering to the individual an effective amount of at least one additional therapeutic agent, e.g., as described below. In certain embodiments, the medicament is for inhibiting or activating a particular molecular pathway and/or mechanism. In certain embodiments, the medicament is for use in a method of inhibiting or activating a particular molecular pathway and/or mechanism in an individual comprising administering to the individual an amount effective of the medicament to inhibit a particular molecular pathway and/or mechanism. An "individual" according to any of the above embodiments can be a human.

In certain embodiments, the present disclosure provides a method for treating a particular disease. In certain embodiments, the method comprises administering to an individual having such disease an effective amount of an antibody fragment. In certain embodiments, the method further comprises administering to the individual an effective amount of at least one additional therapeutic agent, as described below. An "individual" according to any of the above embodiments can be a human.

In certain embodiments, the present disclosure provides a method for inhibiting a particular molecular pathway and/or mechanism in an individual. In certain embodiments, the method comprises administering to the individual an effective amount of an antibody fragment to inhibit a particular molecular pathway and/or mechanism. In certain embodiments, an "individual" is a human.

In certain embodiments, the present disclosure provides pharmaceutical formulations comprising any of the antibody fragments provided herein, e.g., for use in any of the above therapeutic methods. In certain embodiments, a pharmaceutical formulation comprises any of the antibody fragments provided herein and a pharmaceutically acceptable carrier. In certain embodiments, a pharmaceutical formulation comprises any of the antibody fragments provided herein and at least one additional therapeutic agent, e.g., as described below.

Antibody fragments of the present disclosure can be used either alone or in combination with other agents in a therapy. For instance, an antibody fragment of the present disclosure can be co-administered with at least one additional therapeutic agent.

Such combination therapies noted above encompass combined administration (where two or more therapeutic agents are included in the same or separate formulations), and separate administration, in which case, administration of the antibody of the present disclosure can occur prior to, simultaneously, and/or following, administration of the additional therapeutic agent or agents. In certain embodiments, administration of the antibody fragment and administration of an additional therapeutic agent occur within about one month, or within about one, two or three weeks, or within about one, two, three, four, five, or six days, of each other. The antibody fragments described herein can also be used in combination with radiation therapy.

An antibody fragment (and any additional therapeutic agent) can be administered by any suitable means, including parenteral, intrapulmonary, intraocular, and intranasal, and, if desired for local treatment, intralesional administration. Parenteral infusions include intramuscular, intravenous, intraarterial, intraocular, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibody fragments are formulated, dosed and administered in a fashion consistent with good medical practice. Factors for consideration in this context include the particular disease being treated, the particular mammal being treated, the clinical condition of the individual patient, the cause of the disease, the site of delivery of the agent, the method of administration, the scheduling of administration, and other factors known to medical practitioners. The antibody fragment need not be, but is optionally formulated with one or more agents currently used to prevent or treat the disease in question. The effective amount of such other agents depends on the amount of antibody fragment present in the formulation, the type of disease or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody fragment of the present disclosure (when used alone or in combination with one or more other additional therapeutic agents) will depend on the type of disease to be treated, the type of antibody fragment, the severity and course of the disease, whether the antibody fragment is administered for preventive or therapeutic purposes, previous therapy, the patient's clinical history and response to the antibody fragment, and the discretion of the attending physician. The antibody fragment is suitably administered to the patient at one time or over a series of treatments. Depending on the type and severity of the disease, about 1 µg/kg to 15 mg/kg (e.g. 0.1 mg/kg-10 mg/kg) of antibody fragment can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody fragment would be in the range from about 0.05 mg/kg to about 10 mg/kg. Thus, one or more doses of about 0.5 mg/kg, 2.0 mg/kg, 4.0 mg/kg or 10 mg/kg (or any combination thereof) can be administered to the patient. Such doses can be administered intermittently, e.g. every week or every three weeks (e.g., such that the patient receives from about two to about twenty, or e.g., about six doses of the antibody fragment). An initial higher loading dose, followed by one or more lower doses can be administered. The progress of this therapy is easily monitored by conventional techniques and assays.

It is understood that any of the above formulations or therapeutic methods can be carried out using an immunoconjugate in place of or in addition to an antibody fragment of the present disclosure.

F. Immunoconjugates

The presently disclosed subject matter also provides immunoconjugates, which include an antibody fragment, disclosed herein, conjugated to one or more cytotoxic agents, such as chemotherapeutic agents or drugs, growth inhibitory agents, proteins, peptides, toxins (e.g., protein toxins, enzymatically active toxins of bacterial, fungal, plant, or animal origin, or fragments thereof), or radioactive isotopes. For example, an antibody fragment of the disclosed subject matter can be functionally linked (e.g., by chemical coupling, genetic fusion, noncovalent association or otherwise) to one or more other binding molecules, such as another antibody, antibody fragment, peptide or binding mimetic.

In certain embodiments, an immunoconjugate is an antibody-drug conjugate (ADC) in which an antibody fragment is conjugated to one or more drugs, including but not limited to, a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In certain embodiments, an immunoconjugate includes an antibody fragment as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In certain embodiments, an immunoconjugate includes an antibody fragment, as described herein, conjugated to a radioactive atom to form a radioconjugate. A variety of radioactive isotopes are available for the production of radioconjugates. Non-limiting examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When a radioconjugate is used for detection, it can include a radioactive atom for scintigraphic studies, for example tc99m or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

Conjugates of an antibody fragment and cytotoxic agent can be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026. The linker can be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) can be used. Non-limiting examples of linkers are disclosed above.

The immunuoconjugates disclosed herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

G. Articles of Manufacture

In certain embodiments of the present disclosure, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc.

The containers can be formed from a variety of materials such as glass or plastic. The container holds a composition which is by itself or combined with another composition effective for treating, preventing and/or diagnosing the condition and can have a sterile access port (for example the container can be an intravenous solution bag or a vial having a stopper pierceable by a hypodermic injection needle). At least one active agent in the composition is an antibody fragment of the present disclosure. The label or package insert indicates that the composition is used for treating the condition of choice. Moreover, the article of manufacture can comprise (a) a first container with a composition contained therein, wherein the composition comprises an antibody fragment of the present disclosure; and (b) a second container with a composition contained therein, wherein the composition comprises a further cytotoxic or otherwise therapeutic agent. The article of manufacture in this embodiment of the present disclosure can further comprise a package insert indicating that the compositions can be used to treat a particular condition. Alternatively, or additionally, the article of manufacture can further comprise a second (or third) container comprising a pharmaceutically-acceptable buffer, such as bacteriostatic water for injection (BWFI), phosphate-buffered saline, Ringer's solution and dextrose solution. It can further include other materials desirable from a commercial and user standpoint, including other buffers, diluents, filters, needles, and syringes.

It is understood that any of the above articles of manufacture can include an immunoconjugate in place of or in addition to an antibody fragment as described herein.

III. Examples

The following are examples of the methods and compositions of the present disclosure. It is understood that various other embodiments can be practiced, given the general description provided above.

Example 1—Evading the Pre-Existing Anti Hinge Antibody Response by Hinge Engineering Fab and F(ab')$_2$ antibody fragments serve as alternative formats to full-length antibodies in therapeutic and immune assays. They provide the advantage of small size, short serum half-life, and lack of effector function. Several proteases associated with invasive diseases are known to cleave antibodies in the hinge-region and result in anti-hinge antibodies (AHA) towards the neoepitopes. Pre-existing AHA in serum can act as surrogate Fc and reintroduce the properties of the Fc lacking in antibody fragments. While this response is desired during the natural process of fighting disease, it is commonly unwanted for therapeutic antibody fragments. In this study, a truncation in the lower hinge region of the antibody that maintains efficient proteolytic cleavage by IdeS protease was identified. The resulting neoepitope at the F(ab')$_2$ C-terminus did not have detectable pre-existing AHA, providing a practical route to produce F(ab')$_2$ in vitro by proteolytic digestion when pre-existing AHA response is undesired. In this study, the upper hinge region of the antibody was also studied, which provided a detailed analysis of the contribution of C-terminal residues of the upper hinge of human IgG1, IgG2 and IgG4 to pre-existing AHA reactivity in human serum. While no pre-existing antibodies were observed towards the Fab of IgG2 and IgG4 isotype, a significant response was observed towards most residues of the upper hinge of human IgG1. A $T_{225}L$ mutation (also referred to herein as the "$T_{225}L$ variant") and the natural C-terminal $D_{221}$ were identified as solutions with minimal serum reactivity. This study enabled the production of Fab and F(ab')$_2$ fragments for therapeutic and immune assays that have minimal reactivity towards pre-existing AHA.

Materials and Methods

Plasmid Construction and Antibody Expression:

Antibodies were cloned by standard molecular biology techniques into E. coli expression vectors (9, 23) or mammalian expression vectors (24) as previously described. E. coli expression was carried out as described in Simmons et al. (23). IgG and Fab was expressed in 30 mL transient transfection cultures of CHO (25) or HEK293T (26) cells as previously described.

Cloning, Expression, and Purification of IdeS:

IdeS was expressed as N-terminal glutathione S-transferase (GST) fusion protein. The mature sequence of IdeS from Streptococcus pyogenes MGAS1882 (Uniprot ID H8HDR0) was codon optimized for E. coli expression and synthesized by GeneArt™ and cloned by standard molecular biology techniques into E. coli expression vector (23). IdeS was expressed using conditions described in Simmons et al. (23) and purified using glutathione sepharose (GSH) column. Eluate fractions in 50 mM Tris-HCl, pH 8,0, 20 mM glutathione from the GSH column were concentrated and loaded onto 5200 column and eluted with 200 mM $K_2HPO_4$, pH 6.2, 250 mM KCl.

Antibody and Fab Purification:

After expression, the cells were pelleted by gravity. The supernatants were transferred to a 50 ml Falcon tube (Corning, Corning, N.Y., USA). 400 µl of 50% MabSelect SuRe™ protein affinity slurry or Gamma Bind™ Plus slurry (GE Healthcare, Pittsburgh, Pa., USA) was added to the supernatants for IgG and Fab purification respectively. The mixture was incubated overnight at room temperature on an Innova 2000 platform shaker (New Brunswick Scientific, Enfield, Conn., USA). Supernatants were removed and the resin transferred to a 96-well 2 ml filter plate with a 25 µm size membrane (Thompson Instrument, Oceanside, Calif., USA). The resin was washed three times with 1 ml of 1×PBS pH 7.4 by centrifugation at 1,120×g for 5 minutes using a Sorvall™ HT6 Centrifuge (Thermo Scientific, Waltham, Mass., USA). For Fab purification the resin was further washed with 0.2×PBS pH 5.0 before elution. The IgG was eluted using 50 mM phosphoric acid pH 2.9 and the eluate neutralized with 20×PBS pH 11.0 by centrifugation at 1,000×g for 5 minutes. The Fab fragments were eluted using 10 mM sodium citrate pH 2.9 and neutralized with 0.3 M Tris pH 9.0. The eluted IgG and Fab was filtered through 0.2 µm 96-well filter plate (Orochem, Naperville, Ill., USA) by centrifugation at 1,000×g for 5 minutes using an Sorvall HT6 Centrifuge (Thermo Scientific, Waltham, Mass., USA).

IdeS Digestion of IgG Hinge Variants:

IgG at 1 mg/ml was incubated with stated IdeS:IgG ratio (w/w) at 37° C. for 24 hours. For scaled up digestion to generate highly pure F(ab')$_2$ material in large quantities for AHA assays, up to 1:10 IdeS:IgG ratio was used to drive complete digestion.

F(ab')$_2$ Purification after IgG Cleavage by IdeS:

The IdeS cleaved sample was diluted with 25 mM Sodium Acetate, pH 4.4 (Buffer A) and loaded onto a 1 mL SP Sepharose High Performance strong cation exchange column (GE Healthcare, Pittsburgh, Pa., USA) at 150 cm/hr (0.7 cm diameter, 10 cm bed height) equilibrated in Buffer A. The column was washed to baseline with Buffer A and F(ab')$_2$ eluted with a linear salt gradient from 0 to 0.5 M NaCl over 30 column volumes. The eluate was neutralized by addition of 3 M Tris pH 9.0 to adjust the pH to 7.0 and filtered through 0.22 µm STERIFLIP® (EMD Millipore, Billerica, Mass., USA). The SP eluted F(ab')$_2$ was further purified on a MonoS 5/50 GL strong cation exchange column (GE Healthcare, Pittsburgh, Pa., USA) after diluting with Buffer A to lower the conductivity <5 mS/cm. The column was washed to baseline (<0.05 mAU) with Buffer A and the F(ab')$_2$ eluted using a salt gradient from 0 to 0.6 M NaCl over 40 column volumes. The eluted F(ab')$_2$ solution was neutralized with 3 M Tris pH 9.0 to adjust the pH to 7.0 and filtered through 0.22 µm STERIFLIP® (EMD Millipore, Billerica, Mass., USA).

Mass Spectrometry of Fab and F(ab')$_2$ Fragments:

Mass spectrometric data was acquired using an Agilent 6224 TOF LC-MS system (Agilent Technology, Santa Clara, Calif., USA). F(ab')$_2$ was reduced with 100 mM dithiothreitol at 37° C. for 20 minutes. The polypeptide chains were separated with a PLRP-S reversed phase column (Agilent Technologies, Santa Clara, Calif., USA). Intact masses of the reduced light and heavy chains were obtained by Maximun Entropy Deconvolution using MassHunter software (Qualitative Analysis B.03.01).

Analysis of Protein by Capillary Electrophoresis:

All samples were prepared by mixing 5 µl of sample volume with 7 µl of HT Protein Express Sample buffer and incubated for 5 minutes at 70° C. 32 µl of water was added to the samples and centrifuged at 1,000×g for 5 minutes. The chip was prepared according to manufacturer's instructions provided in the LabChip GXII User Guide and samples were analyzed on a Caliper GX II microfluidic system (PerkinElmer® Biotechnology, Waltham, Mass., USA). Samples were analyzed on a Caliper GX II microfluidic system (PerkinElmer® Biotechnology, Waltham, Mass., USA). All reagents were obtained from PerkinElmer®.

Pre-Existing Anti-Hinge Antibody Enzyme-Linked Immunosorbent Assay (ELISA):

MAXISORP® plates (384-well, Nunc, Thermo Fisher Scientific, Rochester, N.Y., USA) were coated with 1 µg/ml F(ab')$_2$ or Fab in 50 mM carbonate, pH 9.6 at 4° C. overnight. Plates were washed with 0.05% polysorbate 20 in PBS, pH 7.4 and then blocked with 0.5% BSA, 15 ppm proclin in PBS, pH 7.4. Pooled human serum from 25 female and 25 male individuals (BioreclamationIVT, Westbury, N.Y., USA) were serially diluted in assay buffer (0.5% BSA, 0.05% polysorbate 20, 15 ppm PROCLIN™, in PBS, pH 7.4) and added to the plates. After a 2 hour incubation, bound pre-existing anti-hinge antibody was detected using horseradish peroxidase (HRP) goat anti-F(ab)$_2$ conjugated anti-human IgG Fc (Jackson ImmunoResearch, West Grove, Pa.) in assay buffer, followed by 3,3',5,5'-tetramethyl benzidine (TMB, Moss Inc., Pasadena, Md., USA) as the substrate. The reaction was stopped with 1 M phosphoric acid and absorbance was read at 450 nm. The absorbance readings at 1:30 dilution were used for the figures to allow presentation of all samples. Comparable results were observed at a 1:10 serum dilution. To calculate the relative AHA reactivity, the titration curve of F(ab')$_2$ was fitted with a 4 parameter curve fitting program (KaleidaGraph, Synerg Software, Reading, Pa.). MidOD (the average OD of the top and bottom OD readings) of the F(ab')$_2$ titration curve was determined. The dilutions of Fab DKTHT (SEQ ID NO: 21) and F(ab')$_2$ corresponding to this midOD were calculated and used to calculate the relative AHA reactivity.

SDS-PAGE and Immunoblots:

For SDS-PAGE, 5 µg of purified F(ab')$_2$ variants and GST-IdeS were mixed with SDS-sample buffer, heated for 5 min at 95° C. and spun for 1 min at 16,000 relative centrifugal force. The samples were loaded onto a NuPAGE 4-12% BisTris/MES gels (Invitrogen). For immunoblotting, 5 ng of protein samples were used for SDS-PAGE. Gels were transferred by IBLOTO (Invitrogen) onto nitrocellulose membrane, immunoblotted with anti-IdeS (Genovis, USA; catalog no. A3-AF1-010, lot no. A3AF1-7C17H) as primary antibody and IRDye800CW conjugated donkey anti-goat antibody (Li-COR®, USA; catalog no. 926-32214, lot no. B80821-03) as the secondary antibody, and imaged with a LI-COR® Odyssey® Imager (LI-COR®, USA). Odyssey® Two-color protein molecular weight marker (LI-COR®, USA) was used for immunoblots and pre-stained SEEBLUEO Plus2 (Invitrogen, USA) was used for Coomassie stained gels.

Protein Stability Measurements by Differential Scanning Fluorimetry:

Protein stability was determined in a Biorad CFX96 TOUCH™ Real-Time System (Biorad, USA) with a final dilution of 1:200 of the SYPRO® Orange dye stock (Molecular Probes™, USA). 1 µl of the SYPRO® Orange dye stock was added to 24 µl of the purified antibody at 100 µg/ml. Fluorescence of the final 25 µl sample in PBS was recorded from 20-100° C. (0.2° C. increments, 10 seconds hold per step).

Results

Fab C-Terminus Determines Response to Pre-Existing AHA:

Originally, reactivity of autoantibodies in human serum towards the upper hinge of Fab molecules was studied with a papain cleaved antibody, abciximab (5). Papain cleavage leaves a C-terminal H224 on the Fab. Later, a more comprehensive study was carried out using biotinylated peptide analogs to dissect the contribution of individual C-terminal residues of the upper hinge (20). In this study, only minimal AHA reactivity towards the upper hinge residues $K_{222}$ through H224 was observed. No signal was observed towards peptides with $T_{225}$ as the C-terminal residue. The use of synthetic peptides can confound results because the Fab-tail spanning the upper hinge residues $D_{221}$ to $T_{225}$ (FIG. 1A) is presented outside of the context of the intact molecule. Thus, the Fab-tail contribution for binding to pre-existing AHA in the setting of an intact Fab was studied.

Figure 1B:
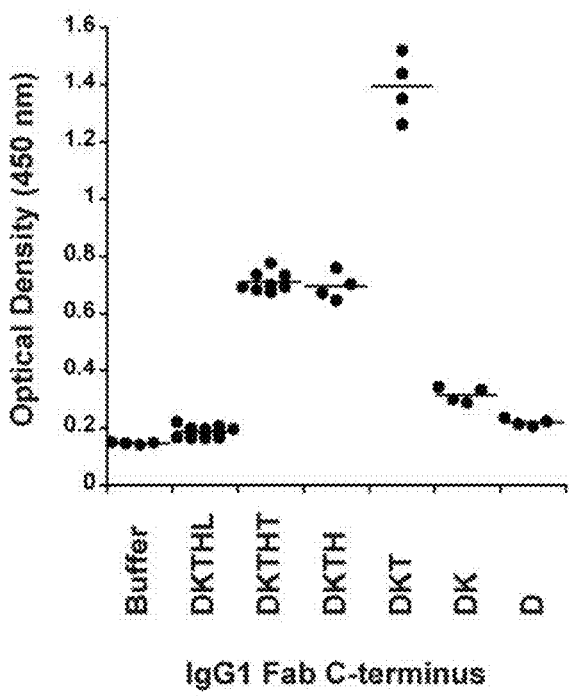

The recombinant expression of Fab molecules in *E. coli* and mammalian cells allows to readily produce molecules with defined C-terminal ends without the need of proteolytic cleavage. To ensure integrity of the C-terminus, correct mass of the purified Fab was confirmed by intact mass-spectrometry. The Fab molecules were coated on microtiter plates, and after incubation with pooled human donor serum, binding of pre-existing AHA was quantified by anti-Fc detection. In agreement with the previous study (20), $T_{223}$ at the C-terminus (having the sequence DKT, also referred to herein as "CDKT" (SEQ ID NO: 17)) showed the highest reactivity of all upper hinge variants towards pre-existing AHA (FIG. 1B). Significant difference to the previous studies is observed with $T_{225}$ at the C-terminus (having the sequence DKTHT (SEQ ID NO: 21), also referred to herein as "CDKTHT" (SEQ ID NO: 14)). This variant did not bind AHA as peptide (20); however, substantial AHA reactivity was observed when tested as Fab. With $D_{221}$ at the C-terminus (having the sequence D, also referred to herein as "CD"), binding of AHA was reduced almost to background. Thus, terminating the Fab at $D_{221}$ provides a solution to minimize recognition by pre-existing AHA while maintaining a natural antibody sequence.

Figure 1C:
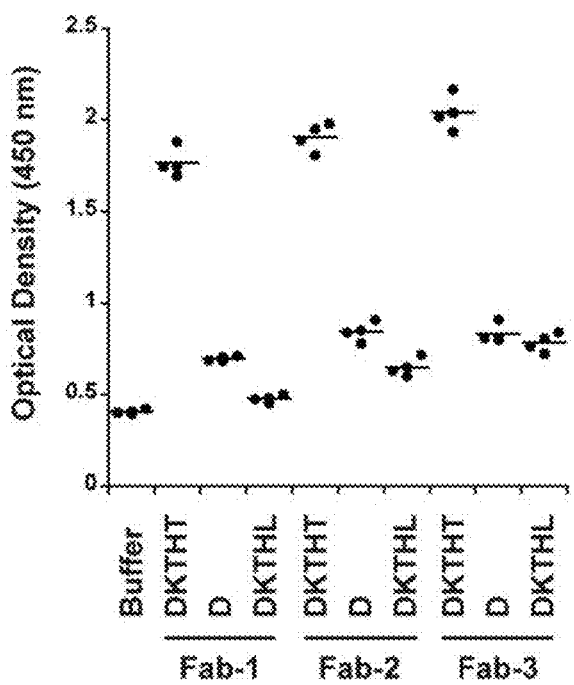
Figure 1D:
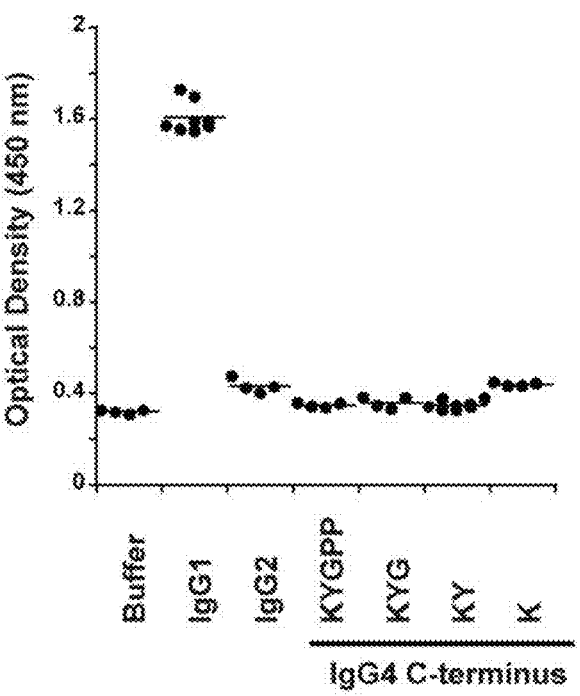

As demonstrated by these experiments, the C-terminal Fab residue has a profound impact on AHA binding. Whether binding by pre-existing antibodies could also be obviated by a single amino acid change at the C-terminus and provide an alternative route to the $D_{221}$ to minimize reactivity towards AHA was investigated. A $T_{225}L$ variant was introduced to place a non-natural residue at the Fab C-terminus, and its binding of AHA was tested. The $T_{225}L$ variant has been described previously (7). The mutation perturbed binding of the pre-existing AHA (FIG. 1B), further highlighting the importance of the C-terminus for binding. To exclude the possibility that the reduced AHA in $T_{225}L$ was due to reduced coating efficiency, an antigen capture format was used to capture the Fab molecules, and a similar fold of AHA signal reduction was also observed. To determine whether this observation can be generalized, three different Fabs were incubated with pooled human serum and binding of pre-existing antibodies was detected by ELISA. Significant signal was observed for the three different Fabs having a DKTHT (SEQ ID NO: 21) C-terminus while reduced binding of pre-existing antibodies to the $D_{221}$ and $T_{225}L$ C-terminus was indeed detected. (FIG. 1C).

Next, Fab molecules of IgG2 and IgG4 isotypes were studied. While IgG1, IgG2 and IgG4 are commonly used for therapeutic antibodies, the use of IgG2 and IgG4 Fabs has not been leveraged for therapeutic development so far. Thus, IgG2 and IgG4 Fabs with the complete upper hinge region (FIG. 1D; C-terminus $K_{218}$ and $P_{225}$, respectively) were tested. In contrast to IgG1 Fab, the IgG2 and IgG4 Fabs were not recognized by pre-existing AHA. Next, the upper hinge of the IgG4 was truncated. The length of the IgG4 isotype upper hinge is shorter when compared to IgG1 (see FIG. 6A-B); however, since the cysteine involved in the heavy-light interchain disulfide is located in the center of the $C_H1$ primary structure, it was able to include residues $K_{218}$ and $Y_{219}$ in the truncation experiments. These truncated upper hinge Fabs displayed a signal similar to the intact IgG1 upper hinge (FIG. 1B).

Figure 7:
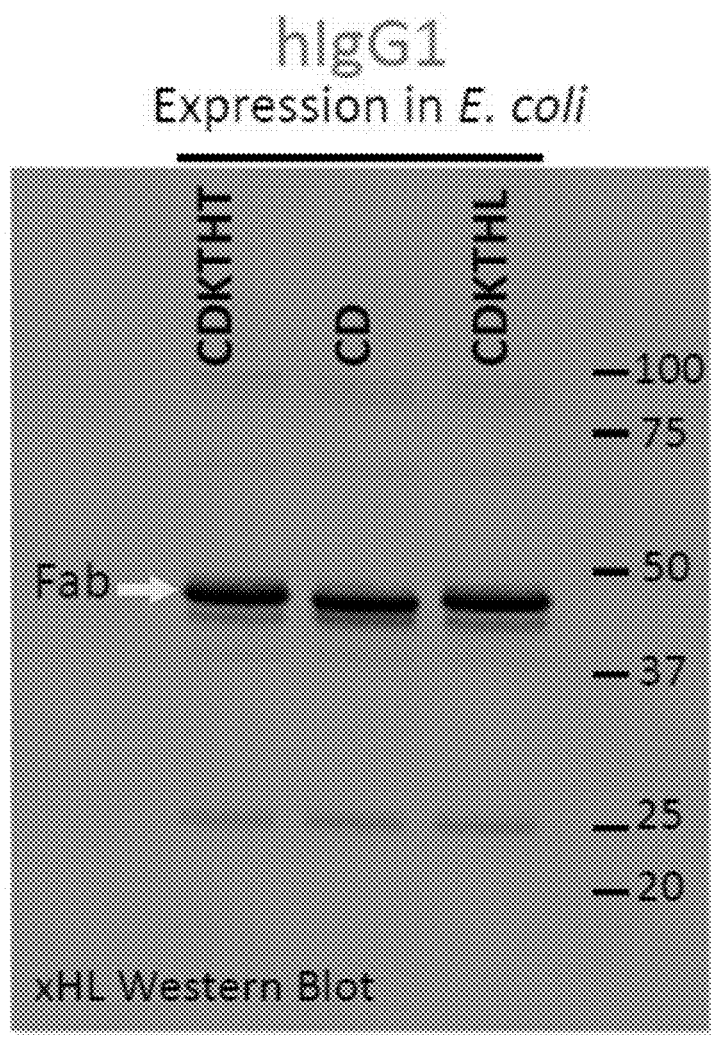
FIG. 7 shows the expression levels of Fabs with upper hinge truncations or mutations in E. coli. Figure discloses SEQ ID NOS 14-15, respectively, in order of appearance.

All Fab molecules within the same isotype yielded similar expression levels in *E. coli* and CHO (FIG. 7). No change in thermal stability was observed within the same isotype (Table 3). Thermal stability of IgG2 and IgG4 Fabs was decreased by about 6° C. compared to IgG1 isotype.

In conclusion, multiple Fab formats with minimal reactivity towards pre-existing AHA exist: IgG1-$D_{221}$, IgG1-$T_{225}L$, IgG2 and IgG4.

TABLE 3

Thermal Stability of T30M Fab determined by differential scanning fluorimetry

| Human isotype | C-terminus | Tm (° C.) |
|---|---|---|
| IgG1 | ..DKTHL (SEQ ID NO: 20) | 81.6 |
|  | ..DKTHT (SEQ ID NO: 21) | 81.8 |
|  | ..DKTH (SEQ ID NO: 27) | 81.7 |
|  | ..DKT | 81.8 |
|  | ..DK | 81.7 |
|  | ..D | 81.9 |
| IgG2 | ..K | 75.5 |
| IgG4 | ..KYGPP (SEQ ID NO: 18) | 75.9 |
|  | ..KYG | 75.7 |
|  | ..KY | 75.8 |
|  | ..K | 75.6 |

IgG1 with the Lower Hinge of IgG2 Cannot be Cleaved Efficiently:

Pre-existing AHA towards the lower hinge region of $F(ab')_2$ have been extensively described in the literature (13, 27). Analogous to the AHA to the upper hinge of Fab molecules, these AHA can act as surrogate Fc or introduce assay artifacts. Thus, development of a $F(ab')_2$ format that impedes AHA binding is desirable. While AHA in serum are found towards $F(ab')_2$ of IgG1 isotype, it has not been possible to establish existence of autoantibodies to the lower hinge of IgG2 isotype. Interestingly, the lack of such autoantibodies coincides with the inability of physiologically relevant human proteases to efficiently cleave IgG2 into $F(ab')_2$ fragments (28). However, inefficient cleavage of IgG2 has been observed using IdeS protease (28). IdeS is an IgG specific endoprotease from *Streptococcus pyogenes* that cleaves after $G_{236}$. In addition to the cleavage site in the antibody hinge region, it recognizes a second site in the Fc that contributes to its high specificity towards IgG (15, 16). The inefficient cleavage of IgG2 antibodies could be caused by the exosite outside of the cleavage site. Thus, the lower hinge residues of IgG2 were grafted onto IgG1 to create an IgG1-2 chimera (FIG. 2B). The cleavage efficiency at different IdeS:IgG ratios was tested (FIG. 2C). While IgG1 wild-type was efficiently cleaved into $F(ab')_2$ at a IdeS:IgG ratio of 1:500, at least 50-fold higher protease concentration was necessary to achieve similar cleavage of the IgG1-2 chimera. It was concluded that the sequence differences in the lower hinge at least partially contribute to the poor cleavage efficiency of IgG2 antibodies. Thus, the IgG1-2 chimera may not be a practical strategy to generate $F(ab')_2$ molecules that do not bind to pre-existing AHA.

Figure 3A:
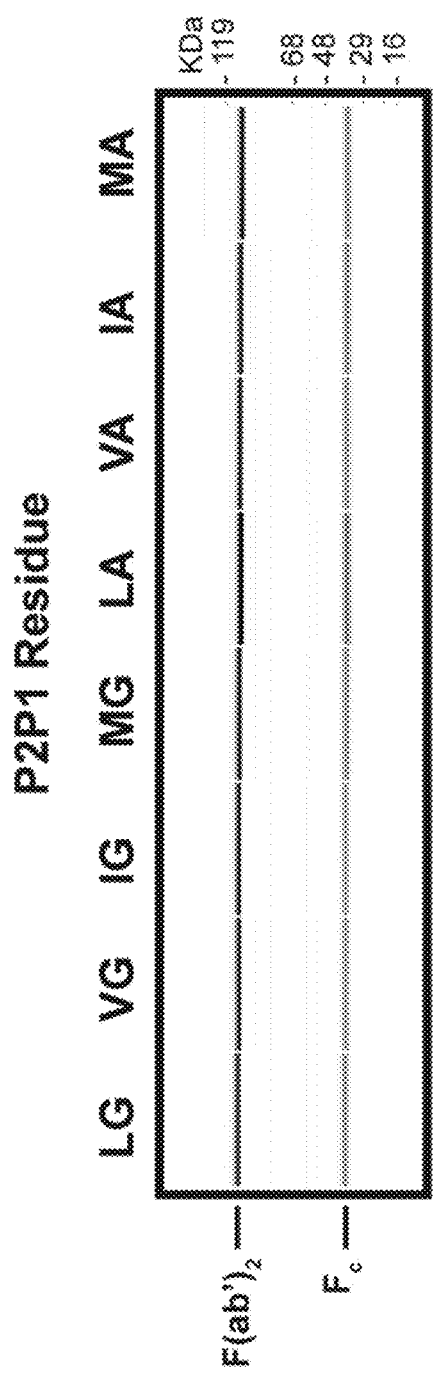
FIGS. 3A-3E show the cleavage of human IgG1 with variants in the P1 and P2 position by IdeS. (3A) Capillary electrophoresis of antibodies with variants at the P1 and P2 position were digested 24 hours at 37° C. with a 1:10 ratio of IdeS:IgG at 1 mg/ml. The P1 and P2 residues are designated in 1-letter code. Leucine and glycine (L235G236) are the natural amino acids at these positions. All antibody variants can be completely cleaved into F(ab')$_2$ fragments. (3B) The cleavage efficiency of the variants was assessed by amount of F(ab')$_2$ produced at different IdeS:IgG ratios. While the variant VG is cleaved comparably to the wild-type sequence (LG), other variants require increased amounts of IdeS for complete digestion. (3C) The cleavage efficiency of the variants was assessed by the amount of F(ab')$_2$ produced at an IdeS:IgG ratio of 1:10. (3D) Schematic diagrams of the expression, purification and screening strategies for the human IgG1 variants.
Figure 3B:
Figure 3C:
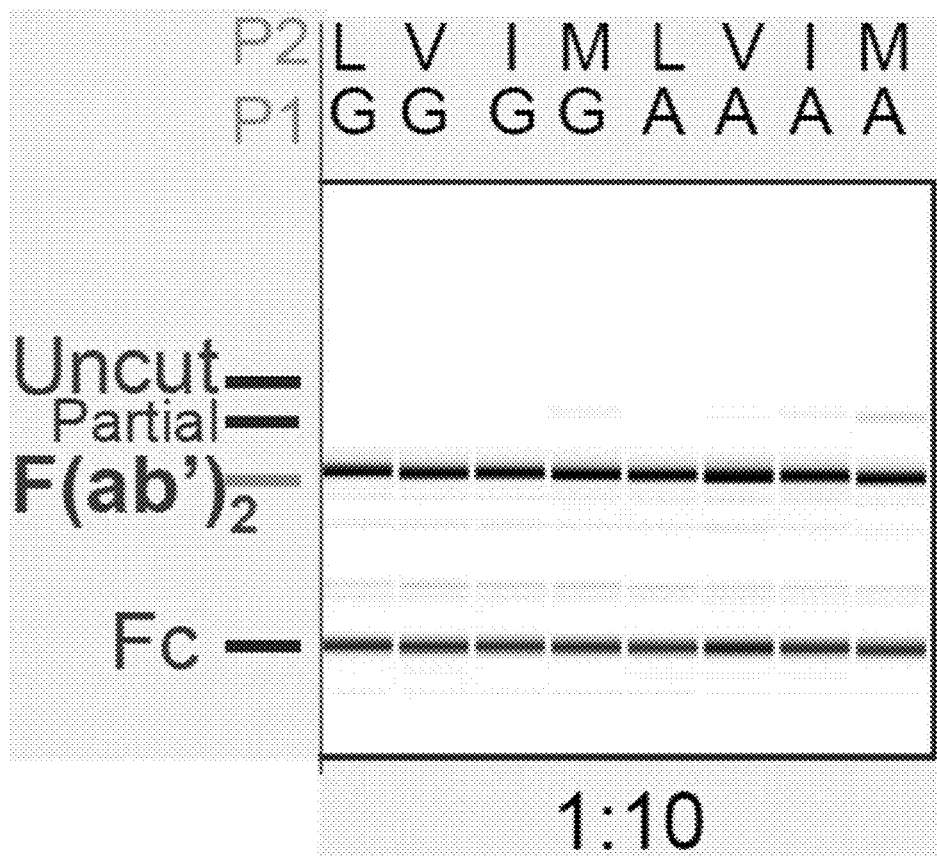
Figure 3D:
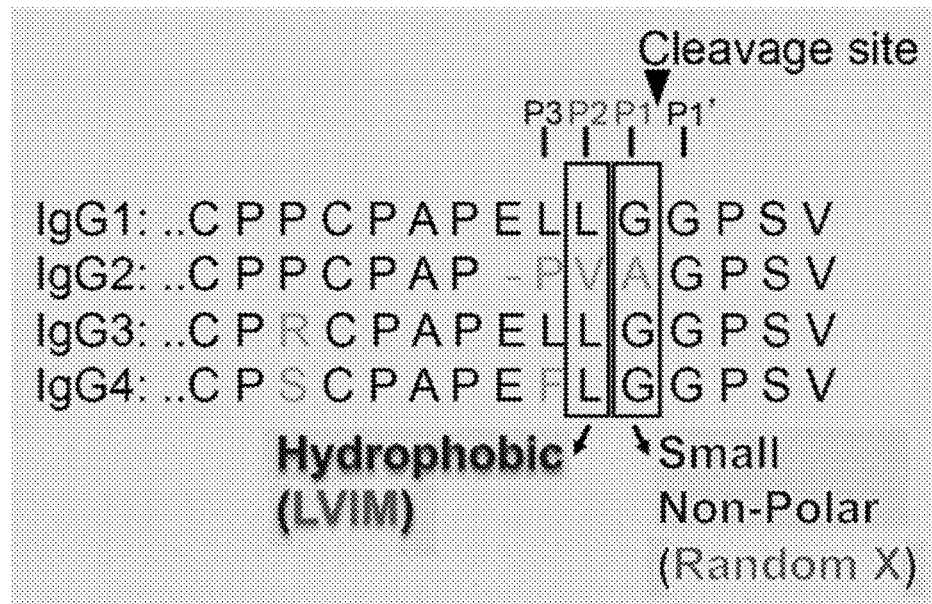
Figure 3E:
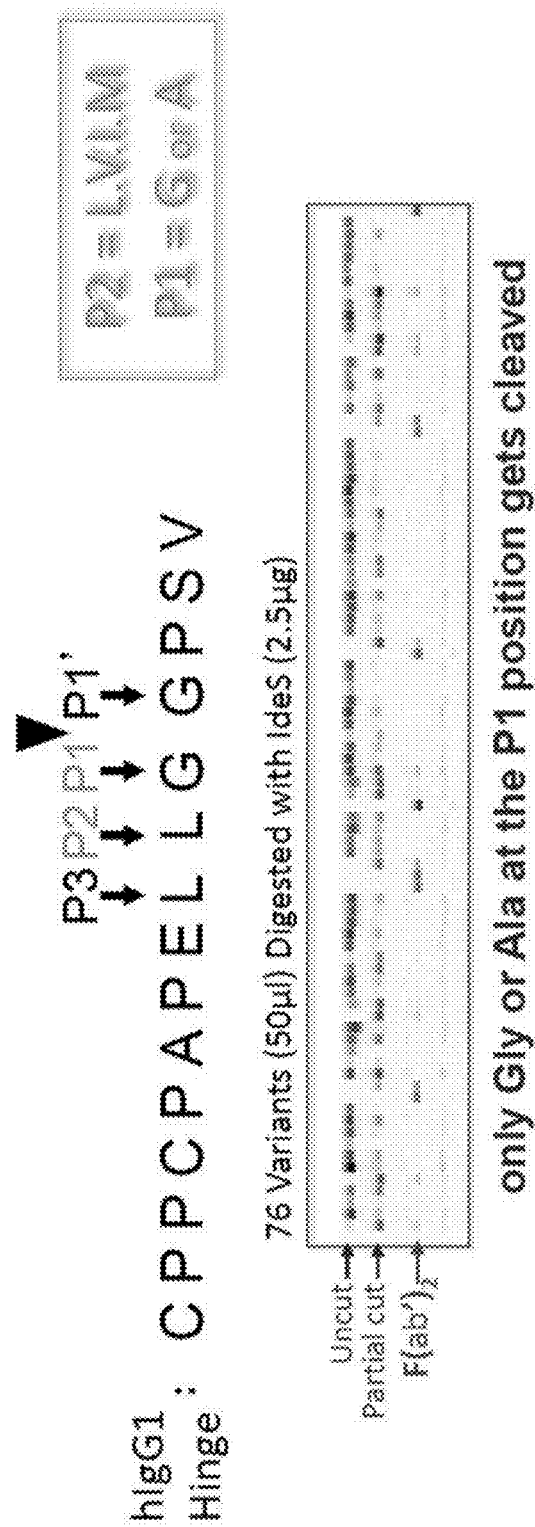

Characterizing the P1 and P2 Positions for Efficient IdeS Cleavage:

It was demonstrated that binding of pre-existing AHA can be prevented by a single C-terminal $T_{225}L$ mutation with the Fab experiments described. A similar strategy was employed for the $F(ab')_2$. As a first step, residues in the P1 (EU236) and P2 (EU235) site that allow cleavage by IdeS protease were identified. A set of 76 Fab variants that included $L_{235}$, $L_{235}V$, $L_{235}I$, or $L_{235}M$ at the P2 position for IdeS were generated and combined with any amino acid except cysteine in P1 (FIGS. 3D and E). The antibodies were purified and digested with IdeS at an IdeS:IgG ratio of 1:10 to identify variants that can be cleaved by IdeS. Such high protease to antibody ratio was chosen to assess proteolysis without taking cleavage efficiency into account. Seven variants were identified that were cleaved by IdeS (FIG. 3A). While the P2 position tolerated all four residues tested, only two amino acids with very small side chains, the natural glycine and alanine, were accepted in the P1 position. This subset was further investigated for cleavage efficiency at three different IdeS:IgG ratios: 1:500, 1:200 and 1:100 (FIG. 3B) and 1:10 (FIG. 3C). The variant $L_{235}V$ in the P2 position demonstrated minimal change in cleavage efficiency compared to the wild-type sequence. All other variants were characterized by a dominant single cleavage at only one side of the hinge, leaving the other side of the antibody intact. While $L_{235}I$ and $L_{235}M$ variants with glycine in the P1 position could be completely cleaved at IdeS:IgG ratio of 1:200, all P2 variants with alanine in P1 needed significantly higher protease amounts. Hence, efficient cleavage by IdeS requires glycine in the P1 position.

C-Terminal $F(ab')_2$ Variants do not Prevent Recognition by Pre-Existing AHA:

IdeS can confound results of the pre-existing AHA assay with a false positive result. This can be explained by binding of serum antibodies by IdeS and their subsequent recognition by the anti-Fc detection antibody. Therefore, it was ensured that $F(ab')_2$ molecules used in the assay did not contain IdeS from the preceding proteolysis reaction. The removal of IdeS in the purified $F(ab')_2$ proteins was confirmed by SDS-PAGE followed by Coomassie staining and anti-IdeS immunoblot (FIG. 4A).

The purified P1 and P2 F(ab')$_2$ variants were then tested for their recognition to pre-existing AHA (FIG. 4B). While there was a reduction of signal compared to the wild-type, none of the antibodies with C-terminal modifications eliminated the reactivity with serum autoantibodies. Changes to the P2 position only had a modest impact. The $G_{236}A$ change in the P1 position reduced the signal to levels comparable to a Fab. Without being limited to a particular theory, it is thus not possible to design a lower hinge with an amino acid variant that retains cleavage by IdeS and concurrently eliminates pre-existing antibody response against the F(ab')$_2$.

Figure 5A:
FIGS. 5A-5F show the reactivity of truncated variants towards pre-existing AHA response. (5A) IdeS cleavage of antibodies with deletions in the IdeS P3, P4, and P5 sites.
Figure 5B:
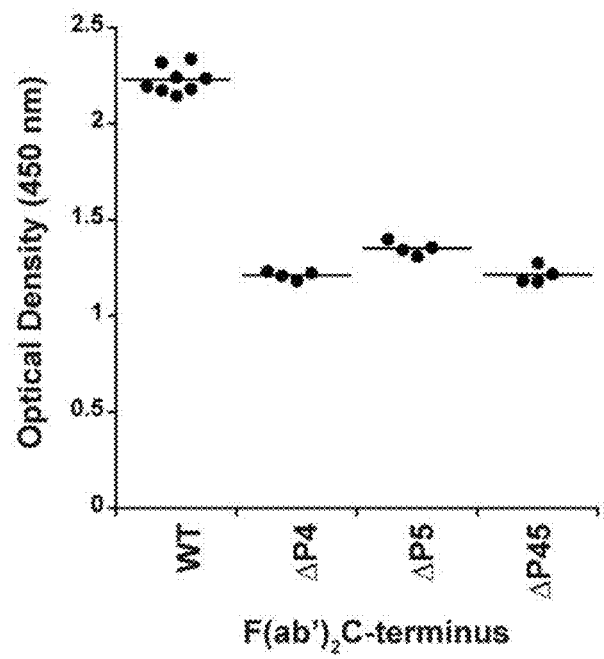
Figure 5C:
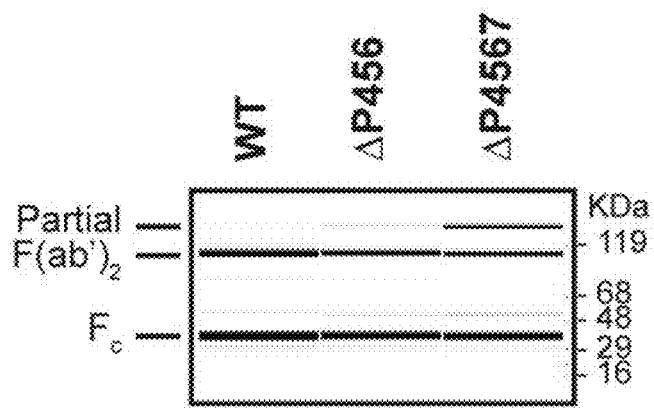
Figure 5D:
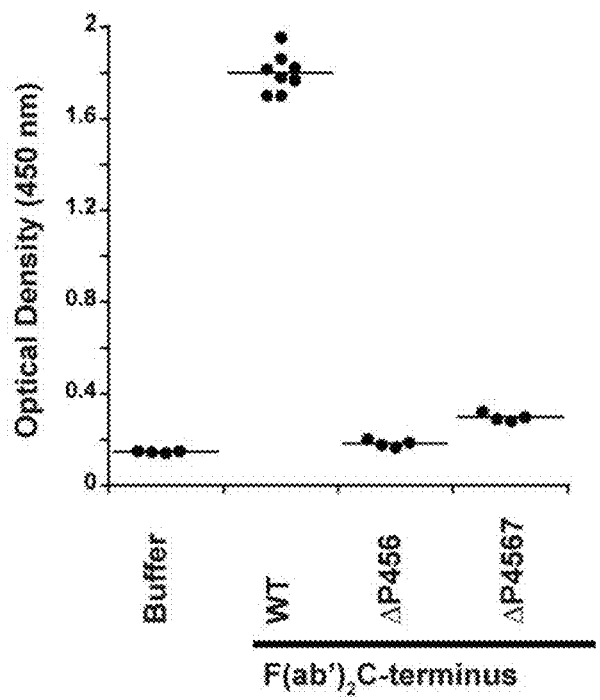
Figure 5E:
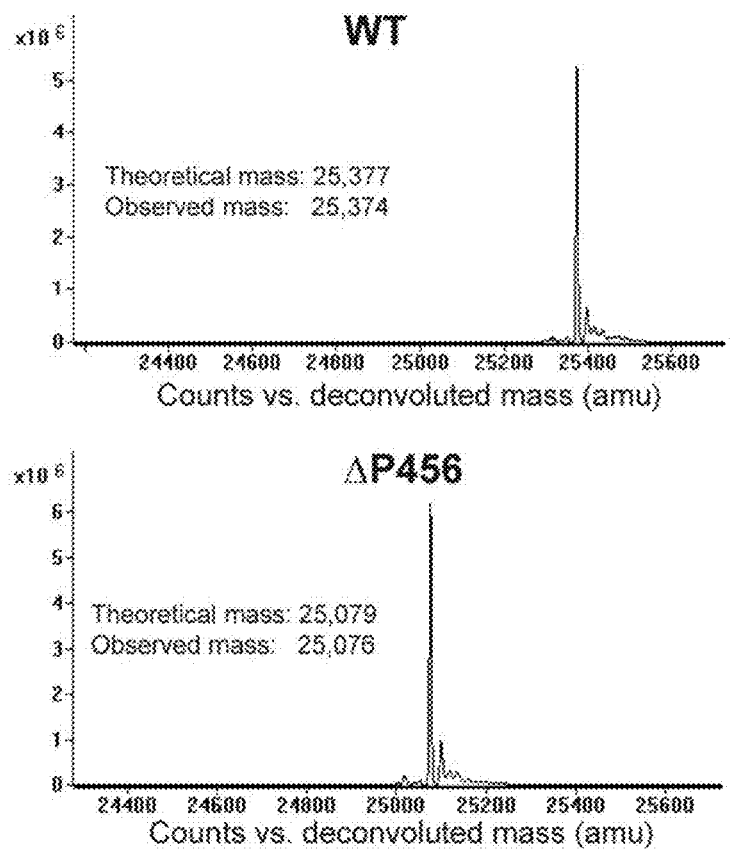
Figure 5F:
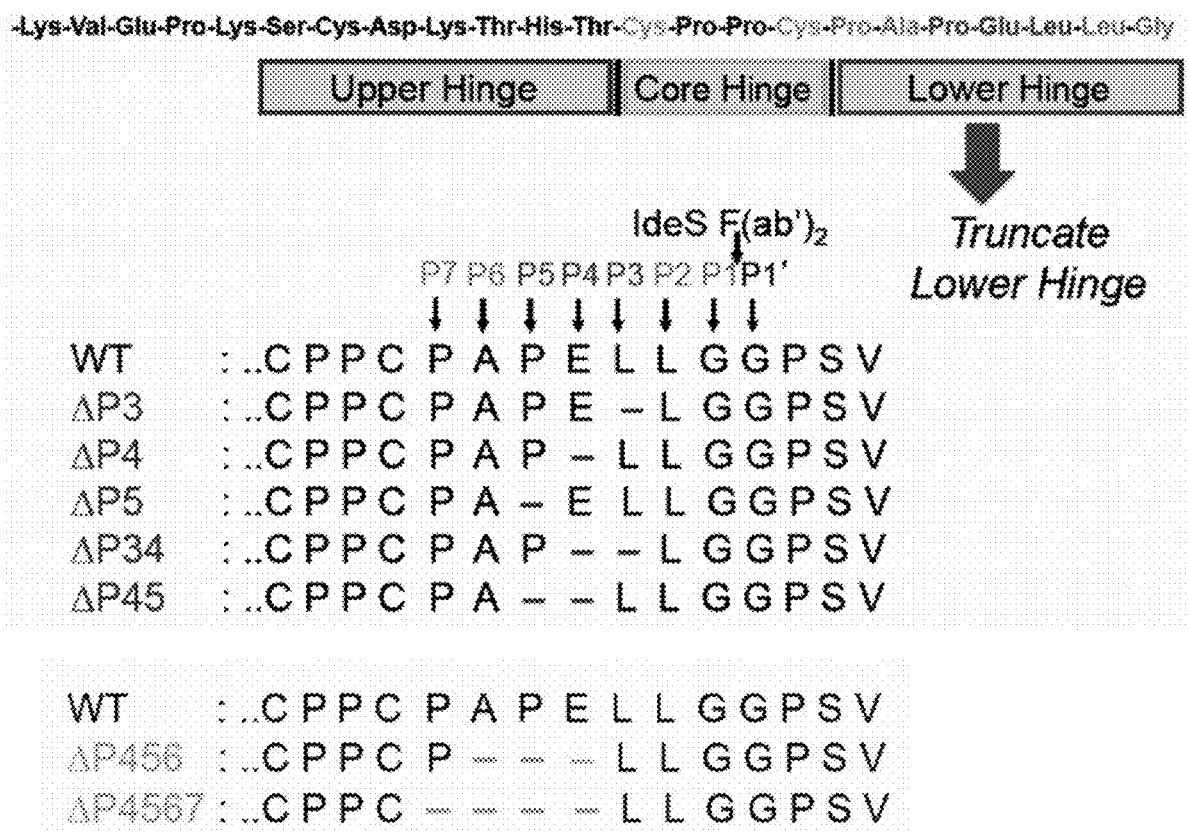
Figure 8:
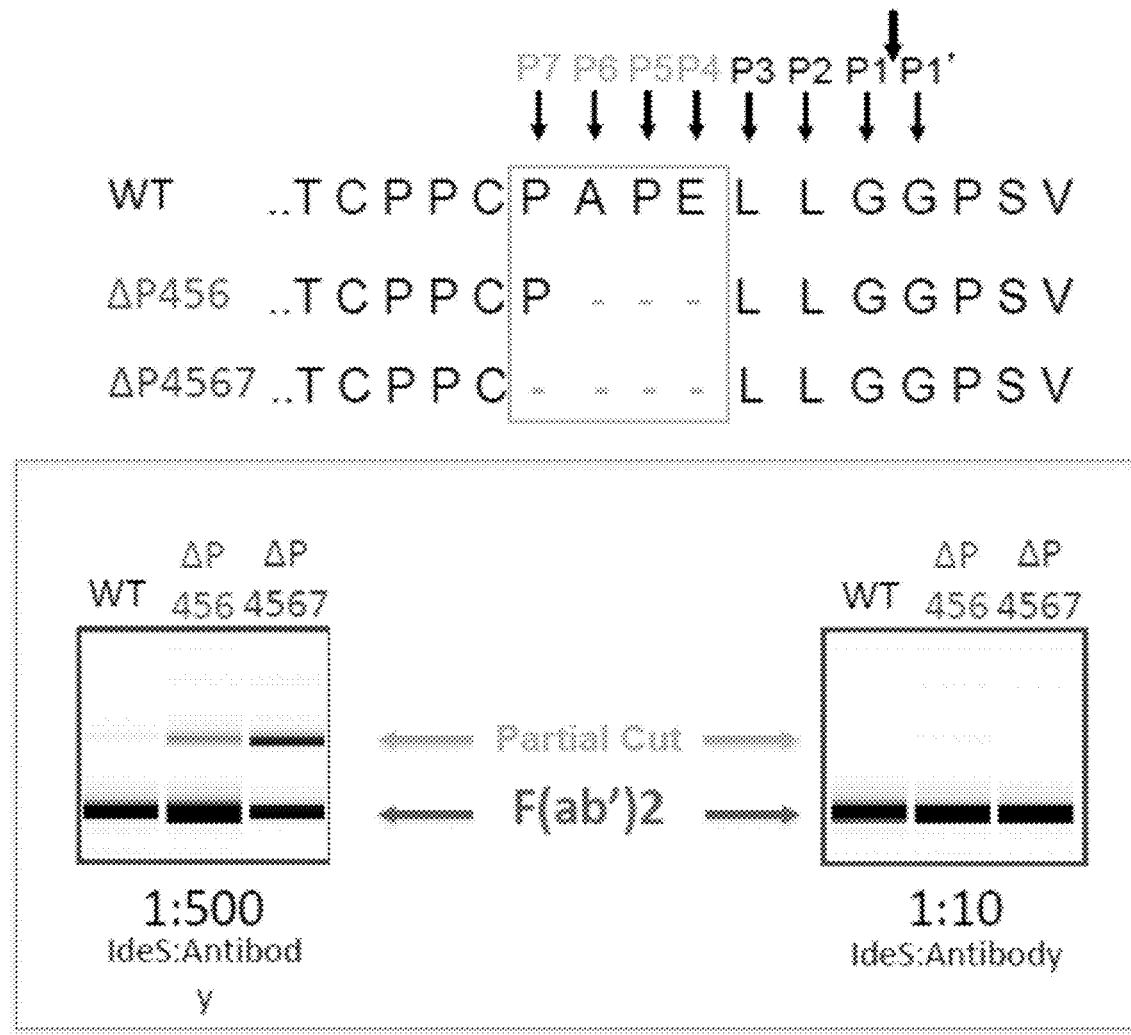
FIG. 8 shows the efficiency of the cleavage of the ΔP456 and ΔP4567 variant produced at an IdeS:IgG ratio of 1:500 or 1:10. Figure discloses SEQ ID NOS 56-58, respectively, in order of appearance.

Deletions in the Lower Hinge Prevents Recognition by Pre-Existing AHA while Retaining IdeS Cleavage:

Another strategy was employed to remove the epitope of the AHA by truncating the lower hinge. Leaving the P1 (EU236) and P2 (EU235) residues untouched for their significance in cleavage efficiency, single and double residue deletions in the P3 (EU234), P4 (EU233) and P5 (EU232) sites of IdeS were generated to identify residues with a minimal impact in cleavage efficiency (see FIG. 5F). Significantly poor cleavage efficiency was observed with deletion of the P3 position, thus this position was not considered for further studies (FIG. 5A). Antibodies with deletions of P4, P5 and a combination of both (ΔP45; also referred to herein as a deletion of amino acid residues at positions EU232-233) were tested for binding to AHA (FIG. 5B). For these variants, a lower signal was observed compared to the wild-type hinge sequence. To further reduce hinge recognition by pre-existing AHA, the deletion was extended to include the P6 (EU231) and P7 (EU230) residues (see FIG. 5F). While the deletion of P4 through P7 sites (ΔP4567; also referred to herein as a deletion of amino acid residues at positions EU230-233) resulted in modestly reduced cleavage efficiency, the deletion of P4 through P6 sites (ΔP456; also referred to herein as a deletion of amino acid residues at positions EU231-233) had cleavage efficiency comparable to wild-type at IdeS:IgG ratio of 1:200 (FIG. 5C and FIG. 8). Both variants did not result in pre-existing AHA recognition (FIG. 5D). To ensure high cleavage specificity of IdeS is maintained, ESI-TOF mass spectrometry was used to analyze the IdeS cleaved F(ab')$_2$. Only a single mass corresponding to the expected cleavage site at $G_{236}$ was observed for the F(ab')$_2$ from the wild-type as well as the ΔP456 variant F(ab')$_2$ (FIG. 5E).

Figure 11:
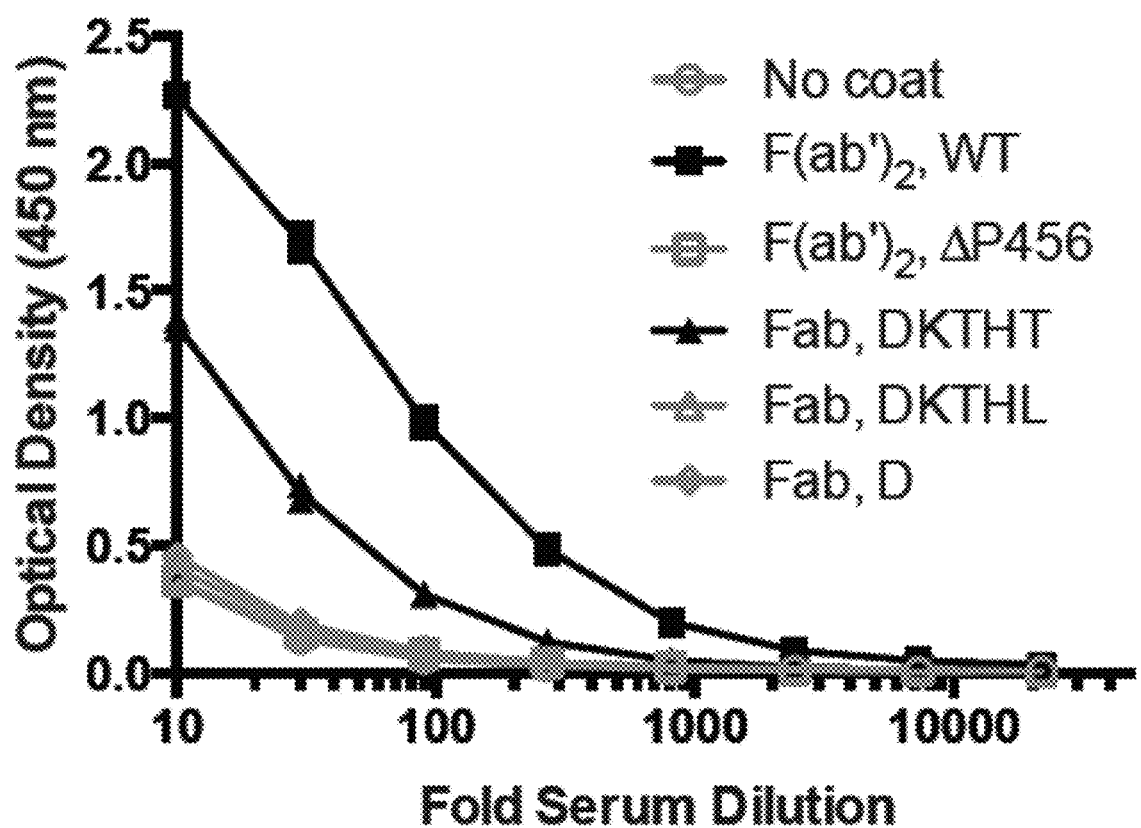
FIG. 11 shows the titration curves of F(ab')$_2$ and Fab molecules in the AHA ELISA. The dilutions corresponding to the OD 450 nm (1.15) at the middle of the F(ab')$_2$ titration curves were 70 and 14 for F(ab')$_2$ and Fab, respectively. Thus, F(ab')$_2$ has five fold higher AHA reactivity than IgG1 Fab. F(ab')$_2$, F(ab')$_2$ ΔP456, Fab T$_{225}$, Fab T$_{225}$L and Fab D$_{221}$ were coated on the wells. Serial dilutions of pooled human serum were added to the wells and control wells were uncoated. Similar results were obtained in 4 other experiments. The data shown here and in FIG. 1B and FIG. 5D were collected from the same experiment. Figure discloses SEQ ID NOS 21 and 20, respectively, in order of appearance.

As shown in FIG. 11, the observed AHA binding signal of the ΔP456 variant F(ab')$_2$ is comparable to the two Fab C-terminal variants, Fab $D_{221}$ and Fab $T_{225}L$. The dilutions corresponding to the OD (1.15) at the middle of the F(ab')$_2$ titration curves were 70 and 14 for F(ab')$_2$ and Fab, respectively. Without being limited to a particular theory, the five-fold higher AHA activity seen with F(ab')$_2$ compared to Fab $T_{225}$ can be explained by the potential bivalent binding of AHA to the F(ab')$_2$, which indicates that F(ab')$_2$ molecules need avoid pre-existing AHA. To exclude the possibility that the reduced AHA reactivity seen in F(ab')$_2$ ΔP456 and Fab $T_{225}L$ was due to reduced coating efficiency, an antigen capture format was used to detect AHA. The OD readings (n=4) were 2.2±0.1, 0.34±0.03, 1.3±0.1, 0.36±0.02 and 0.32±0.01 on antigen coated wells receiving F(ab')$_2$, ΔP456 F(ab')$_2$, Fab, Fab $T_{225}L$ and buffer at 1:30 serum dilution, respectively. Thus, these results confirmed that ΔP456 F(ab')$_2$ and Fab $T_{225}L$ had reduced AHA reactivity compared to their corresponding wild type molecules.

These data show that the ΔP456 variant provides a solution to avoid pre-existing AHA response towards the lower hinge of F(ab')$_2$ while maintaining the possibility to produce the F(ab')$_2$ antibody fragment by the well-established route of proteolytic digest.

Figure 9A:
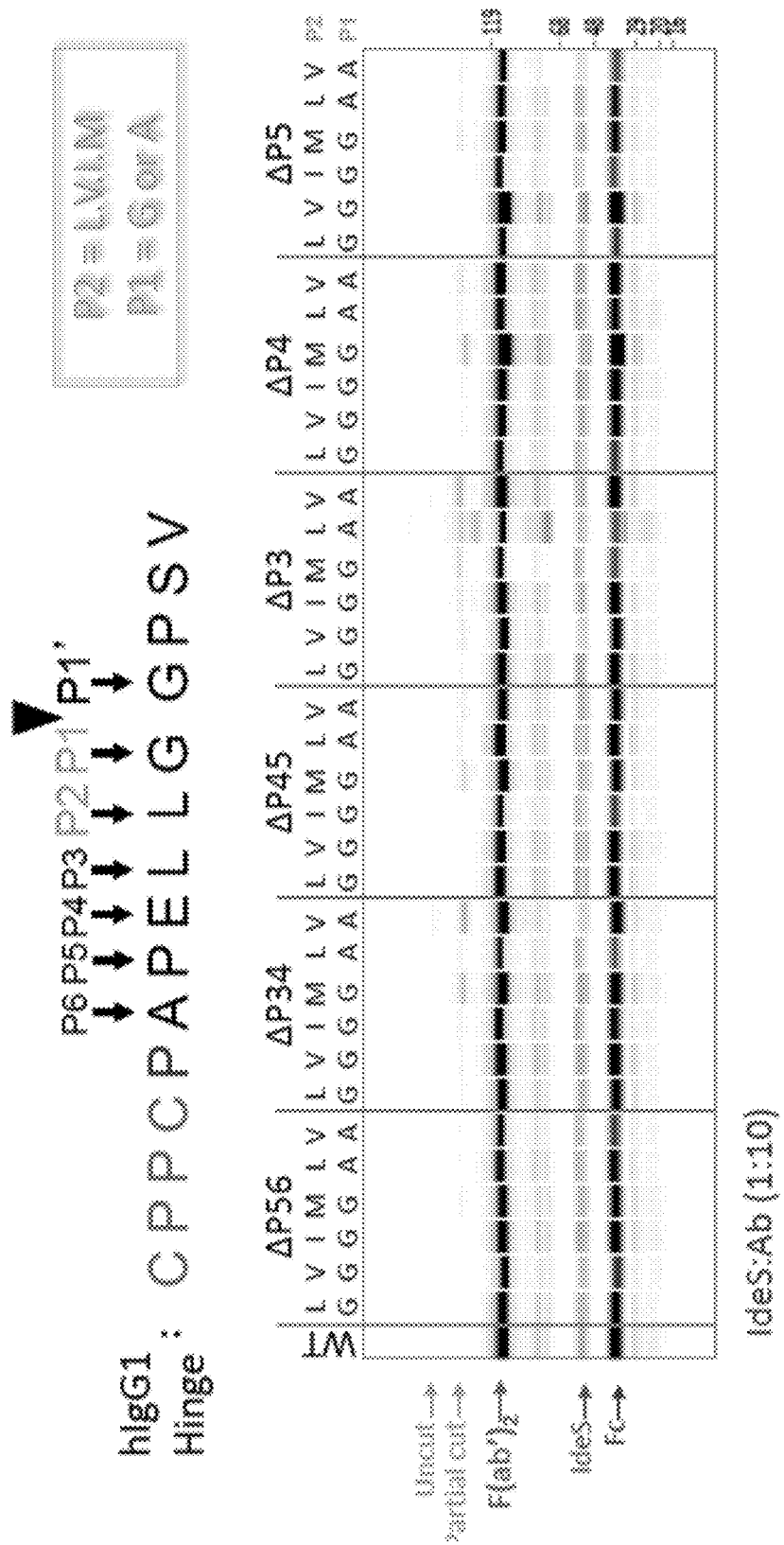
Figure 9B:
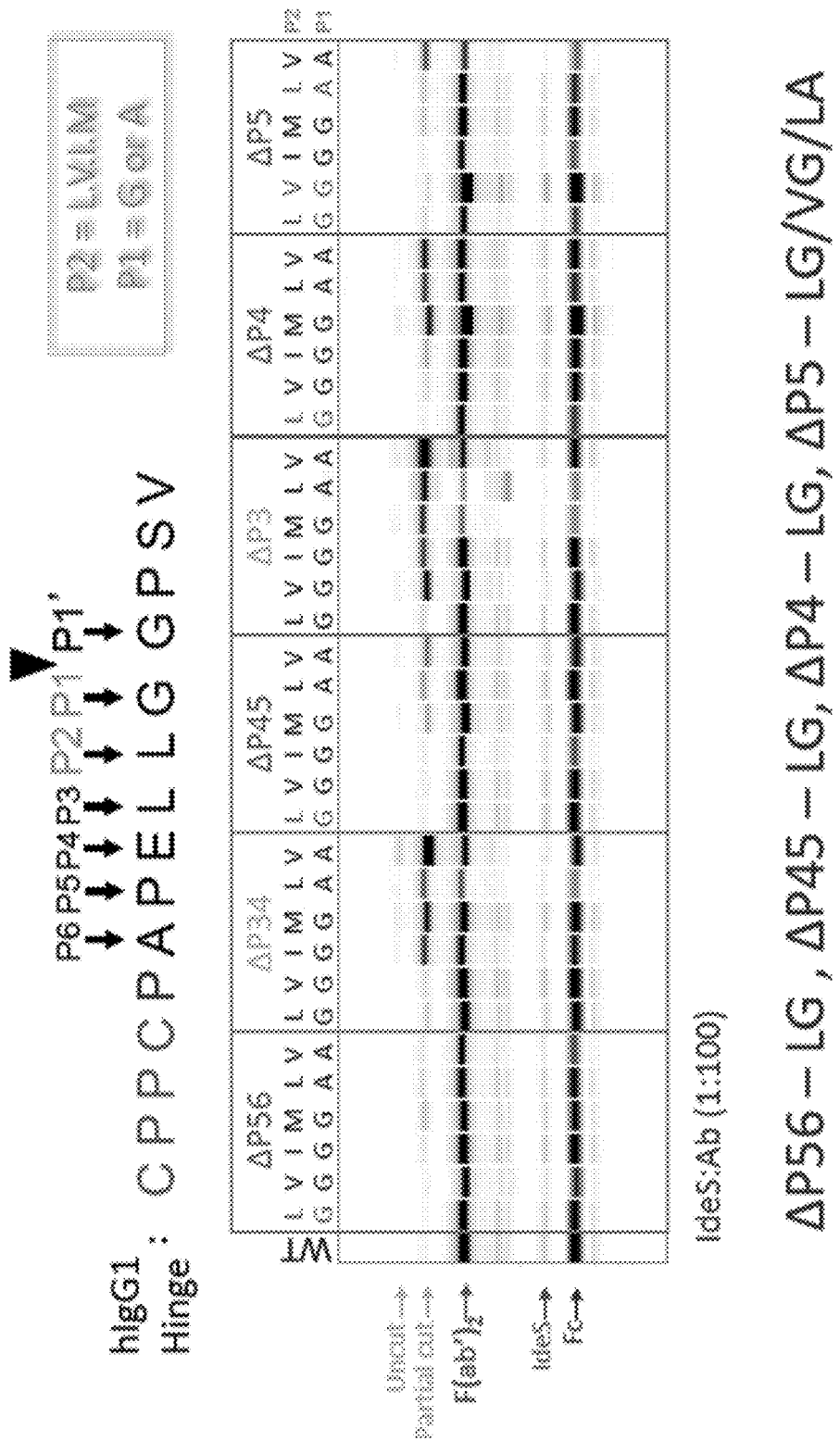
Figure 9C:
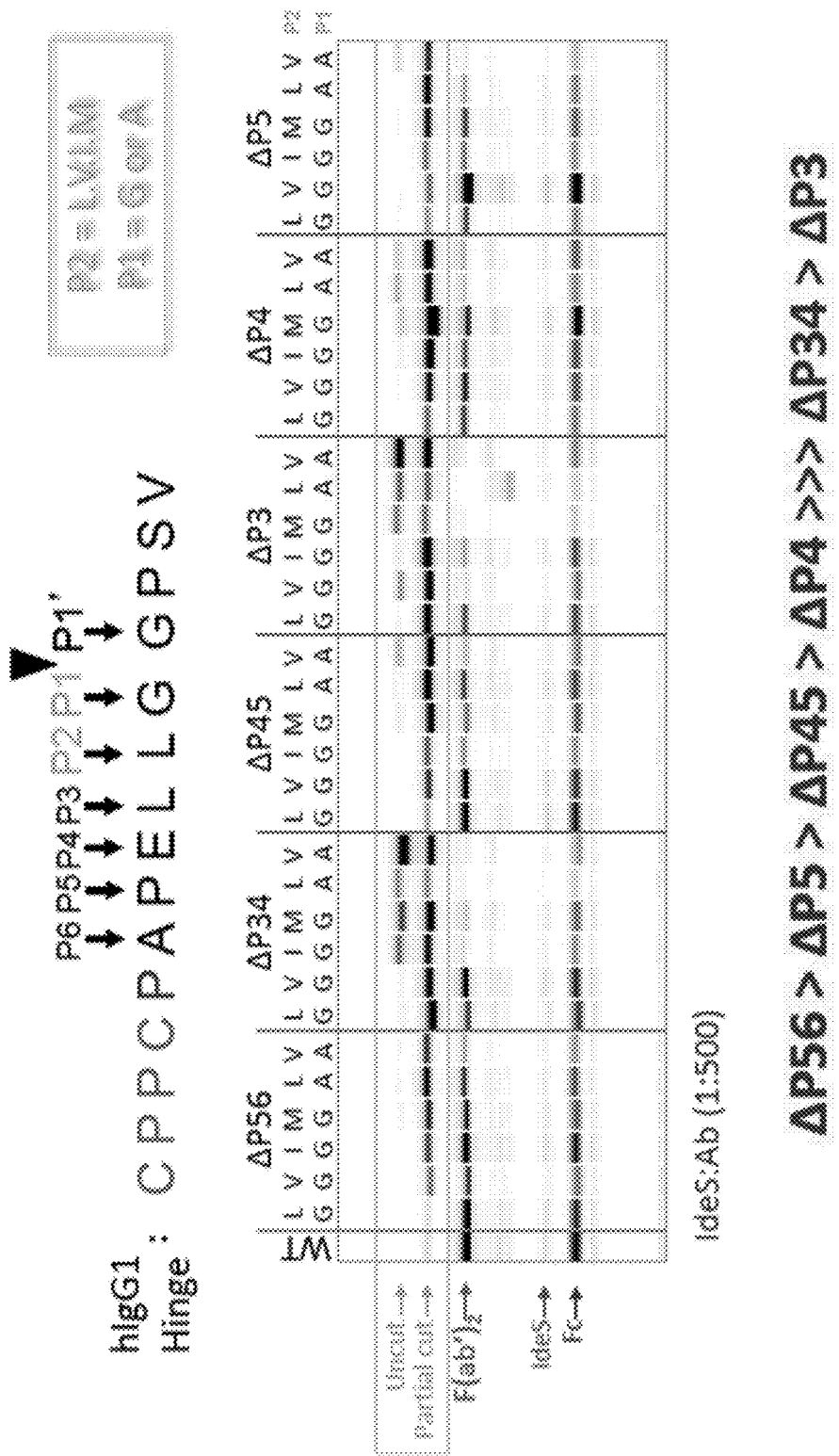
Figure 10A:
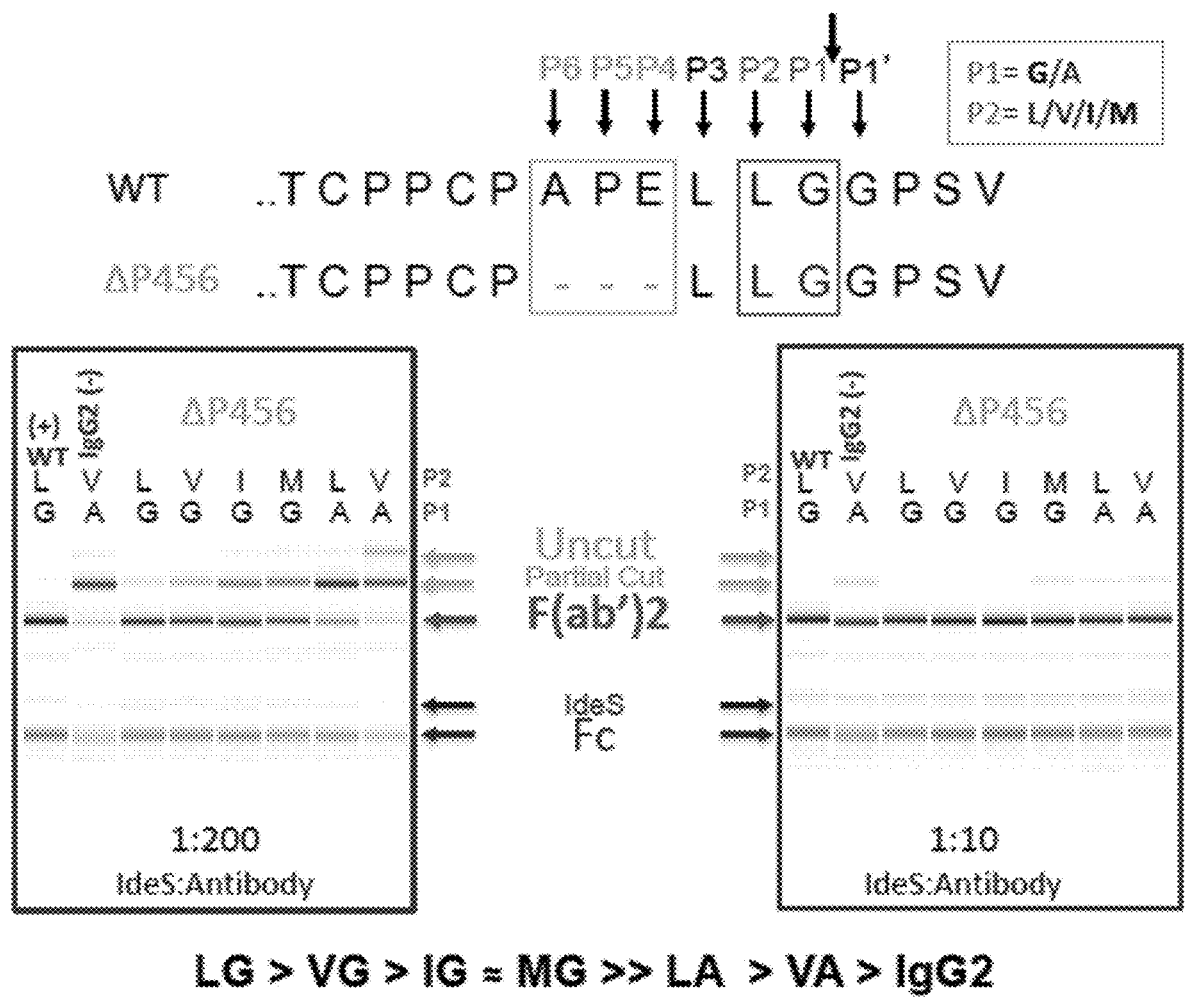
FIGS. 10A-10B show the reactivity of the ΔP456 and ΔP4567 variants with modified P1 and P2 residues to pre-existing AHA. (10A) The cleavage efficiency of the variants was assessed by amount of F(ab')$_2$ produced at an IdeS:IgG ratio of 1:10 and 1:200.
Figure 10B:
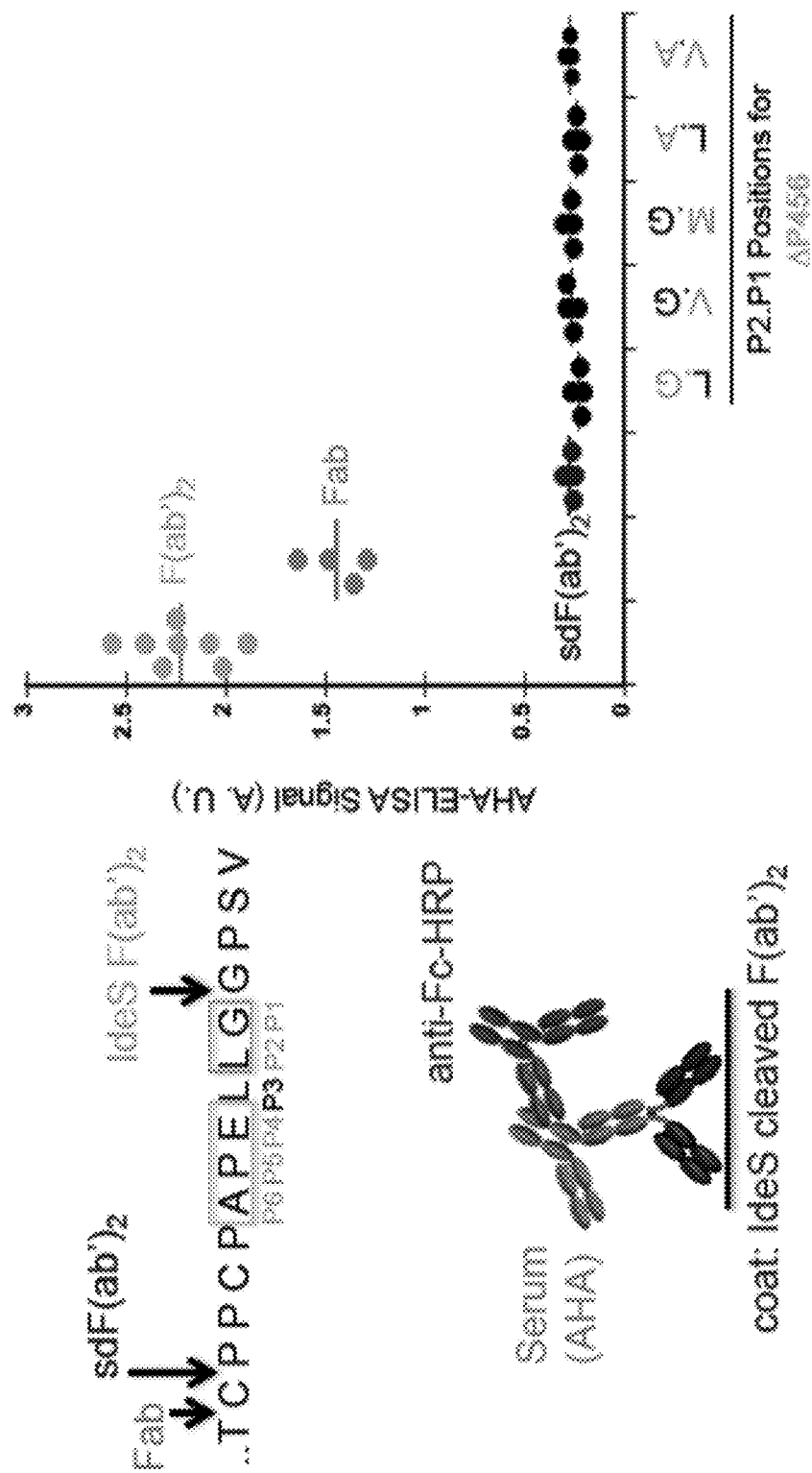

Deletions in the Lower Hinge in C-Terminal F(ab')$_2$ Variants:

The C-terminal variants having deletions in the lower hinge region were analyzed to determine whether the recognition by pre-existing AHA were altered. A set of 6 variants that included $L_{235}$, $L_{235}V$, $L_{235}I$, or $L_{235}M$ at the P2 position for IdeS with alanine or glycine at P1 were generated with various hinge region deletions (FIG. 9). This subset was further investigated for cleavage efficiency at three different IdeS:IgG ratios: 1:10 (FIG. 9A), 1:100 (FIG. 9B) and 1:500 (FIG. 9C). As shown in FIG. 9D, the variant $L_{235}V$ or $G_{236}A$ in combination with a deletion at P5, resulted in a reduced AHA signal compared to the deletion of P5 alone. As shown in FIG. 10, the ΔP456 variant that included $L_{235}V$, $L_{235}I$, or $L_{235}M$ at P2 position with alanine or glycine in P1 exhibited similar reductions in AHA signal compared to ΔP456 alone (FIG. 10B); however, the deletion of ΔP456 alone exhibited better cleavage efficiency compared to the variants in combination with ΔP456 (FIG. 10A).

Discussion

Antibody fragments such as Fab and F(ab')$_2$ are attractive therapeutic formats when a short systemic half-life and an effector-silent molecule are concurrently desired. Certain fragments are also natural products of proteases associated with invasive diseases such as tumor cells and bacteria and are generated in an effort to evade immune surveillance. As a consequence, the C-terminal neoepitope of the Fab and F(ab')$_2$ fragment is recognized by the immune system and result in AHA that can provide surrogate Fc.

In this study, the reactivity of pre-existing AHA towards the individual C-terminal residues spanning the upper hinge region of human IgG1, IgG2 and IgG4 isotype was dissected. While it was previously reported that pre-existing AHA did not exist towards neoepitopes in the lower hinge of IdeS-cleaved human IgG2 antibodies, reactivity towards the upper hinge of human isotypes was incompletely investigated so far. In this study, pre-existing AHA towards the upper hinge of IgG2 and IgG4 isotype was not detected. This in turn may suggest that these isotypes are not the target of proteases of invasive diseases. This can be explained by the effector-attenuated nature of these isotypes and the fact that removing the Fc region of these isotypes does not provide an advantage for tumors and bacteria. In contrast, IgG1 isotype seems to be the prime target for these proteases. Indeed, several proteases have been described to cleave in the upper hinge of human IgG1, including plasmin, human neutrophil elastase and LysC. This study shows that pre-existing AHA exist towards all cleavage sites of the upper hinge of human IgG1 with the exception of $D_{221}$. Without being limited to a particular theory, the absence of AHA toward $D_{221}$ may be a reflection of the inability of human proteases to cleave after this residue or the inability to raise antibodies toward this neoepitope. The highest reactivity was observed towards the C-terminal $T_{223}$ Fab. Interestingly, this C-terminus coincides with the cleavage point of human neutrophil elastase, a protease that is secreted by neutrophils and macrophages during inflammation to destroy bacteria and host tissue (29).

Pre-existing AHA can rapidly recruit effector-function to a molecule that is designed to be effector-less. Using a Fab of IgG2 or IgG4 isotype can provide one strategy to supply a molecule without pre-existing antibody response. Alternatively, introducing a non-natural residue at the heavy chain C-terminus, like the $T_{225}L$ mutation, or truncating the upper hinge to $D_{221}$ is a strategy for the IgG1 isotype. While the $T_{225}L$ mutation eliminates the response towards pre-existing AHA, it implies that in principle, it can elicit an immune response as well. This is further supported by a recent study with an anti-TNFR1 domain antibody (34). The addition of a C-terminal alanine was sufficient to reduce binding of pre-existing human anti-$V_H$ antibodies during screening in vitro; however, one subject was found to develop high levels of antibodies specific toward the modified C-terminus in a Phase I clinical trial. In addition, potential exopeptidase activity on a longer tail can eventually result in a neoepitope that is recognized by pre-existing AHA. Removing the unstructured upper hinge altogether like the Fab-$D_{221}$ further minimizes the risk of such secondary responses. This is supported by the crystal structure of an anti-hinge antibody that has been crystalized in complex with a peptide spanning the IdeS-cleaved lower hinge of human IgG1 (30). The peptide is bound to the antibody in an extended conformation, suggesting that truncating the upper or lower hinge can successfully remove the neoepitope and suppress an immune response for antibodies against the hinge region.

These findings can also have implications on the design of studies in cynomolgus monkeys. While the lower hinge region is highly conserved between cynomolgus and human IgG, considerable differences exist in the upper hinge region (31) that will prevent cross-species reactivity. This may have an impact on toxicological studies in cynomolgus as liabilities from pre-existing AHA towards a human Fab cannot be addressed by these studies.

Beyond therapeutic use, the Fab-$D_{221}$ can also be considered for the recombinant expression of Fab for crystallographic studies, since the upper hinge is not commonly resolved in crystal structures due to the unstructured nature. This example demonstrates that equal stability and expression can be achieved with a Fab-$D_{221}$ construct. Eliminating the unstructured areas may further improve crystallization outcomes.

The most efficient route to generate F(ab')$_2$ molecules so far is by proteolytic digest and proteases with high-specificity such as IdeS are preferred. As discussed earlier, pre-existing AHA also exist towards the lower hinge of F(ab')$_2$ molecules. The AHA titer towards IdeS-cleaved antibody is higher compared to a Fab. Without being limited to a particular theory, this may be due to the bivalent nature of the F(ab')$_2$ that provides an avidity based binding component in the assay or a natural higher abundance of F(ab')$_2$ that lead to increased titers. Several strategies were employed to remove the AHA reactivity while maintaining cleavage efficiency by IdeS.

Since the C-terminal residue has an important role in epitope recognition (22), the first strategy was to mutate the C-terminal residue of the F(ab')$_2$ to remove binding activity of AHA. However, this was not possible due to the strict requirement of glycine in the P1-position for efficient cleavage by IdeS. The selected set of mutations in the P2-site had only modest impact on AHA binding, further confirming the importance of the C-terminal residue for reactivity with AHA. The coinciding differences in AHA binding with the IdeS cleavage efficiency of the P1 and P2 variants perhaps explains the reason why the IgG2 isotype with valine in P2 and alanine in P1 position is less susceptible to anti-hinge antibody response. The requirement for glycine in position P1 for efficient cleavage is accompanied by the high conservation of this residue within different isotypes and across species.

By deleting three residues in the lower hinge (ΔP456), it was able to maintain the cleavage efficiency of IdeS while removing pre-existing AHA recognition. It demonstrates that positions upstream of the P3 site have minor relevance for efficient cleavage. In addition to removing the reactivity towards pre-existing AHA, truncating the lower hinge can dampen an immune response towards this epitope. Based on structural studies, an AHA binds the lower hinge in an extended conformation and the five C-terminal residues interact with the antibody complementarity determining regions (CDR) (30). By removing three residues from the lower hinge, only 4 residues remained after IdeS cleavage. This short sequence may not be sufficient for a robust immune response and may reduce the likelihood of developing de novo antibodies toward the engineered hinge.

Pre-existing antibodies have also been demonstrated to decrease effector-function (32) in vitro and can also confound immunogenicity assays during drug development. While the majority of anti-therapeutic antibodies (ATAs) towards a humanized antibody are targeting the idiotype, rheumatoid factor, a low affinity antibody towards the Fc region has been described. One way to eliminate artifacts by rheumatoid factor in the immunogenicity assay is to use an antibody fragment devoid of the Fc region. However, it is import to use fragments that are not recognized by other pre-existing antibodies. These findings provide multiple Fab formats and a F(ab')$_2$ format that can fulfill these criteria.

In summary, by choosing the appropriate antibody fragment, it is possible to evade recognition by pre-existing AHA. For Fab molecules, several options exist: (1) using an IgG2 or IgG4 isotype, (2) a mutation of the C-terminal residue ($T_{225}L$), or (3) terminating the Fab with residue $D_{221}$. Options are more limited for F(ab')$_2$ molecules due to the need for proteolytic digestion. A deletion was identified in the lower hinge of IgG1, however, that maintains high cleavage efficiency and specificity and removes reactivity with pre-existing AHA. Using these formats can enable further minimization of safety concerns with antibody fragments in a therapeutic setting and remove interference in assay development.

Example 2—F(Ab)$_2$ ΔP456 has Reduced AHA Mediated FcγRIIIa and C1q Binding

It has been previously described that purified AHA antibodies can act as surrogate Fc and restore ADCC/CDC function that was lost by IdeS generated F(ab')$_2$ (20, 22). To study if the reduced binding of AHA by the disclosed engineered Fab and F(ab')$_2$ variants is further reflected by reduced recruitment of Fcγ receptors and C1q, bridging experiments were employed. To assess binding of AHA to FcγRIIIa, human serum was added to Fab or F(ab')$_2$ coated wells and incubated for 2 hours as described above. After the plates were washed, soluble FcγRIIIa(V158)-His-GST (consisting of the extracellular domain fused with Gly-His6-glutathione-S-transferase ("Gly-His6" disclosed as SEQ ID NO: 28) at the carboxy-terminus) was added at 0.5 µg/ml. Bound FcγRIIIa(V158)-His-GST was detected using horseradish peroxidase-conjugated mouse anti-His antibody (Penta-His (SEQ ID NO: 29), Qiagen, Germantown, Md.) followed by TMB as the substrate. To assess binding of AHA to human C1q, human serum was added to Fab or F(ab')$_2$ coated wells and incubated for 2 hours as described above. After the plates were washed, purified human C1q (Quidel, San Diego, Calif.) was added. Bound C1q was detected with goat anti-C1q antibody (Nordic Immunological Laboratories, Tilburg, The Netherlands) followed by rabbit anti-goat IgG-HRP (Jackson ImmunoResearch, West Grove, Pa.) and TMB as the substrate.

Significant binding of FcγRIIIa and C1q for F(ab')$_2$ was observed while little signal was detected for the ΔP456 F(ab')$_2$ variant, indicating that the engineering of the F(ab')$_2$ variant significantly reduced the risk of ADCC/CDC activation. The OD readings (n=3) were 0.45±0.05, 0.10±0.02 and 0.09±0.02 for FcγRIIIa binding and 0.98±0.09, 0.158±0.004 and 0.107±0.009 for C1q binding on F(ab')$_2$, ΔP456 variant, and uncoated wells at 1:10 diluted serum, respectively.

IV. References

1. Desjarlais, J. R., and Lazar, G. A. (2011) Modulation of antibody effector function. *Experimental Cell Research.* 317, 1278-1285.
2. Olafsen, T. (2012) Fc engineering: serum half-life modulation through FcRn binding. *Methods Mol Biol.* 907, 537-556.
3. Gadkar, K., Pastuskovas, C. V., Le Couter, J. E., Elliott, J. M., Zhang, J., Lee, C. V., Sanowar, S., Fuh, G., Kim, H. S., Lombana, T. N., Spiess, C., Nakamura, M., Hass, P., Shatz, W., Meng, Y. G., and Scheer, J. M. (2015) Design and Pharmacokinetic Characterization of Novel Antibody Formats for Ocular Therapeutics. *Invest. Ophthalmol. Vis. Sci.* 56, 5390-5400.
4. Walsh, G. (2014) Biopharmaceutical benchmarks 2014. *Nat Biotechnol.* 32, 992-1000.
5. Curtis, B. R., Swyers, J., Divgi, A., McFarland, J. G., and Aster, R. H. (2002) Thrombocytopenia after second exposure to abciximab is caused by antibodies that recognize abciximab-coated platelets. *Blood.* 99, 2054-2059.
6. Porter, R. R. (1950) The formation of a specific inhibitor by hydrolysis of rabbit antiovalbumin. *Biochem J.* 46, 479-484.
7. Chen, Y., Wiesmann, C., Fuh, G., Li, B., Christinger, H. W., McKay, P., de Vos, A. M., and Lowman, H. B. (1999) Selection and analysis of an optimized anti-VEGF antibody: crystal structure of an affinity-matured fab in complex with antigen. *J. Mol Biol.* 293, 865-881.
8. Spiess, C., Zhai, Q., and Carter, P. J. (2015) Alternative molecular formats and therapeutic applications for bispecific antibodies. *Mol. Immunol.* 67, 95-106.
9. Carter, P., Kelley, R. F., Rodrigues, M. L., and Snedecor, B. (1992) High level *Escherichia coli* expression and production of a bivalent humanized antibody fragment. *Nature.* 10.1038/nbt0292-163.
10. Kostelny, S. A., Cole, M. S., and Tso, J. Y. (1992) Formation of a bispecific antibody by the use of leucine zippers. *J Immunol.* 148, 1547-1553.
11. Glennie, M. J., McBride, H. M., Worth, A. T., and Stevenson, G. T. (1987) Preparation and performance of bispecific F(ab' gamma)2 antibody containing thioether-linked Fab" gamma fragments. *J Immunol.* 139, 2367-2375.
12. Ellerman, D., and Scheer, J. M. (2011) Generation of bispecific antibodies by chemical conjugation (Kontermann, R. E. ed), pp. 47-63, Springer-Verlag Berlin Heidelberg, 10.1007/978-3-642-20910-9_3.
13. Brerski, R. J., and Jordan, R. E. (2010) Cleavage of IgGs by proteases associated with invasive diseases: an evasion tactic against host immunity? *MAbs.* 2, 212-220.
14. Nisonoff, A., Wissler, F. C., and Lipman, L. N. (1960) Properties of the major component of a peptic digest of rabbit antibody. *Science.* 132, 1770-1771.
15. Pawel-Rammingen, von, U., Johansson, B. P., and Bjŏrck, L. (2002) IdeS, a novel streptococcal cysteine proteinase with unique specificity for immunoglobulin G. *EMBO J.* 21, 1607-1615.
16. Vincents, B., Pawel-Rammingen, von, U., Bjorck, L., and Abrahamson, M. (2004) Enzymatic characterization of the streptococcal endopeptidase, IdeS, reveals that it is a cysteine protease with strict specificity for IgG cleavage due to exosite binding. *Biochemistry.* 43, 15540-15549.
17. Osterland, C. K., Harboe, M., and Kunkel, H. G. (1963) Anti-gamma-globulin factors in human sera revealed by enzymatic splitting of anti-Rh antibodies. *Vox Sang.* 8, 133-152.
18. Mellbye, O. J., and Natvig, J. B. (1971) Evidence for immune complexes containing antibody to the pepsin site of IgG in rheumatoid synovial fluids. *Clin Exp Immunol.* 8, 889-899.
19. Terness, P., Kohl, I., Hübener, G., Battistutta, R., Moroder, L., Welschof, M., Dufter, C., Finger, M., Hain, C., and Jung, M. (1995) The natural human IgG anti-F(ab')2 antibody recognizes a conformational IgG1 hinge epitope. *J Immunol.* 154, 6446-6452.
20. Brerski, R. J., Luongo, J. L., Petrone, D., Ryan, M. H., Zhong, D., Tam, S. H., Schmidt, A. P., Kruszynski, M., Whitaker, B. P., Knight, D. M., and Jordan, R. E. (2008) Human anti-IgG1 hinge autoantibodies reconstitute the effector functions of proteolytically inactivated IgGs. *J Immunol.* 181, 3183-3192.
21. Rispens, T., de Vrieze, H., de Groot, E., Wouters, D., Stapel, S., Wolbink, G. J., and Aarden, L. A. (2012) Antibodies to constant domains of therapeutic monoclonal antibodies: anti-hinge antibodies in immunogenicity testing. *J Immunol Methods.* 375, 93-99.
22. Brerski, R. J. Kinder, M., Grugan, K. D., Soring, K. L., Carton, J., Greenplate, A. R. Petley, T., Capadi, D., Brosnan, K., Emmell, E., Watson, S., and Jordan, R. E. (2014) A monoclonal antibody against hinge-cleaved IgG restores effector function to proteolytically inactivated IgGs in vitro and in vivo. *MAbs.* 6(5):1265-1273.
23. Simmons, L. C., Reilly, D., Klimowski, L., Raju, T. S., Meng, G., Sims, P., Hong, K., Shields, R. L., Damico, L. A., Rancatore, P., and Yansura, D. G. (2002) Expression of full-length immunoglobulins in *Escherichia coli*: rapid and efficient production of aglycosylated antibodies. *J Immunol Methods.* 263, 133-147
24. Eaton, D. L., Wood, W. I., Eaton, D., Hass, P. E., Hollingshead, P., Wion, K., Mather, J., Lawn, R. M., Vehar, G. A., and Gorman, C. (1986) Construction and characterization of an active factor VIII variant lacking the central one-third of the molecule. *Biochemistry.* 25, 8343-8347.
25. Wong, A. W., Baginski, T. K., and Reilly, D. E. (2010) Enhancement of DNA uptake in FUT8-deleted CHO cells for transient production of afucosylated antibodies. *Biotechnol Bioeng.* 106, 751-763.
26. Bos, A. B., Duque, J. N., Bhakta, S., Farahi, F., Chirdon, L. A., Junutula, J. R., Harms, P. D., and Wong, A. W. (2014) Development of a semi-automated high throughput transient transfection system. *Journal of Biotechnology.* 180, 10-16.
27. Van Schie, K. A., Wolbink, G.-J., and Rispens, T. (2015) Cross-reactive and pre-existing antibodies to therapeutic antibodies-Effects on treatment and immunogenicity. *MAbs.* 7, 662-671.
28. Brerski, R. J., Oberholtzer, A., Strake, B., and Jordan, R. E. (2011) The in vitro resistance of IgG2 to proteolytic attack concurs with a comparative paucity of autoantibodies against peptide analogs of the IgG2 hinge. *MAbs.* 3, 558-567.
29. Belaaouaj, A., Kim, K. S., and Shapiro, S. D. (2000) Degradation of outer membrane protein A in *Escherichia coli* killing by neutrophil elastase. *Science.* 289, 1185-1188
30. Malia, T. J., Teplyakov, A., Brerski, R. J., Luo, J., Kinder, M., Sweet, R. W., Almagro, J. C., Jordan, R. E., and Gilliland, G. L. (2014) Structure and specificity of an antibody targeting a proteolytically cleaved IgG hinge. *Proteins.* 10.1002/prot.24545.
31. Jacobsen, F. W., Padaki, R., Morris, A. E., Aldrich, T. L., Armitage, R. J., Allen, M. J., Lavallee, J. C., and Arora, T. (2011) Molecular and Functional Characterization of Cynomolgus Monkey IgG Subclasses. *J Immunol.* 186, 341-349.
32. Jones, J. D., Shyu, I., Newkirk, M. M., and Rigby, W. F. C. (2013) A rheumatoid factor paradox: inhibition of rituximab effector function. Arthritis Res. Ther. 15, R20.
33. Pollack, C. V., Reilly, P. A., Eikelboom, J., Glund, S., Verhamme, P., Bernstein, R. A., Dubiel, R., Huisman, M. V., Hylek, E. M., Kamphuisen, P. W., Kreuzer, J., Levy, J. H., Sellke, F. W., Stangier, J., Steiner, T., Wang, B., Kam, C.-W., and Weitz, J. I. (2015) Idarucizumab for Dabigatran Reversal. *N. Engl. J. Med.* 373, 511-520.
34. Cordy, J. C., Morley, P. J., Wright, T. J., Birchler, M. A., Lewis, A. P., Emmins, R., Chen, Y. Z., Powley, W. M., Bareille, P. J., Wilson, R., Tonkyn, J., Bayliffe, A. I., and Lazaar, A. L. (2015) Specificity of human anti-variable heavy (VH) chain autoantibodies and impact on the design and clinical testing of a VH domain antibody antagonist of TNF-α receptor 1. *Clin Exp Immunol.* 10.1111/cei.12680.

Although the foregoing compositions and methods have been described in some detail by way of illustration and example for purposes of clarity of understanding, the descriptions and examples should not be construed as limiting the scope of the instant disclosure. The disclosures of all patent and scientific literature cited herein are expressly incorporated in their entirety by reference.

What is claimed is:

1. A composition comprising an isolated antibody fragment, wherein the antibody fragment has reduced or no reactivity towards pre-existing anti-hinge antibodies, wherein the antibody fragment is a F(ab')$_2$ that comprises a C-terminus deletion at position EU231.

2. A composition comprising an isolated antibody fragment, wherein the antibody fragment has reduced or no reactivity towards pre-existing anti-hinge antibodies, wherein the antibody fragment is a F(ab')$_2$ that comprises a C-terminus deletion at positions EU231-232.

3. A composition comprising an isolated antibody fragment, wherein the antibody fragment has reduced or no reactivity towards pre-existing anti-hinge antibodies, wherein the antibody fragment is a F(ab')$_2$ that comprises a C-terminus deletion at positions EU231-233.

4. A composition comprising an isolated antibody fragment, wherein the antibody fragment has reduced or no reactivity towards pre-existing anti-hinge antibodies, wherein the antibody fragment is a F(ab')$_2$ that comprises a C-terminus deletion at positions EU231-234.

5. A composition comprising an isolated antibody fragment, wherein the antibody fragment has reduced or no reactivity towards pre-existing anti-hinge antibodies, wherein the antibody fragment is a F(ab')$_2$ that comprises a C-terminus deletion at positions EU230-234.

6. A pharmaceutical formulation comprising the composition of claim 1 and a pharmaceutically acceptable carrier.

7. A pharmaceutical formulation comprising the composition of claim 2 and a pharmaceutically acceptable carrier.

8. A pharmaceutical formulation comprising the composition of claim 3 and a pharmaceutically acceptable carrier.

9. A pharmaceutical formulation comprising the composition of claim 4 and a pharmaceutically acceptable carrier.

10. A pharmaceutical formulation comprising the composition of claim 5 and a pharmaceutically acceptable carrier.

* * * * *